United States Patent
Wang

(10) Patent No.: US 11,486,862 B2
(45) Date of Patent: Nov. 1, 2022

(54) ULTRASOUND IMAGE DISPLAY METHOD AND APPARATUS, STORAGE MEDIUM, AND ELECTRONIC DEVICE

(71) Applicant: TENCENT TECHNOLOGY (SHENZHEN) COMPANY LIMITED, Shenzhen (CN)

(72) Inventor: Liang Wang, Shenzhen (CN)

(73) Assignee: TENCENT TECHNOLOGY (SHENZHEN) COMPANY LIMITED, Shenzhen (CN)

(*) Notice: Subject to any disclaimer, the term of this patent is extended or adjusted under 35 U.S.C. 154(b) by 258 days.

(21) Appl. No.: 16/935,421

(22) Filed: Jul. 22, 2020

(65) Prior Publication Data

US 2020/0348268 A1 Nov. 5, 2020

Related U.S. Application Data

(63) Continuation of application No. PCT/CN2019/082216, filed on Apr. 11, 2019.

(30) Foreign Application Priority Data

May 24, 2018 (CN) .......................... 201810508663.2

(51) Int. Cl.
*G01N 29/46* (2006.01)
*G01N 29/06* (2006.01)
(Continued)

(52) U.S. Cl.
CPC .......... *G01N 29/46* (2013.01); *G01N 29/0609* (2013.01); *G06F 17/14* (2013.01); *A61B 8/466* (2013.01)

(58) Field of Classification Search
CPC ..... G01N 29/46; G01N 29/0609; G06F 17/14
See application file for complete search history.

(56) References Cited

U.S. PATENT DOCUMENTS

2016/0238568 A1   8/2016   Feleppa et al.

FOREIGN PATENT DOCUMENTS

| CN | 101061961 A | 10/2007 |
| CN | 103512960 A * | 1/2014 |

(Continued)

OTHER PUBLICATIONS

L. Wang, P. R. Girard, A. Bernard, Z. Liu, P. Clarysse, et al.. 3-D biquaternionic analytic signal and application to envelope detection in 3-D ultrasound imaging. 2nd International Conference on 3D Imaging, Dec. 2012, Liège, Belgium, pp. 1-8, (Year: 2012).*

(Continued)

*Primary Examiner* — Regis J Betsch
(74) *Attorney, Agent, or Firm* — Crowell & Moring LLP

(57) ABSTRACT

This present disclosure describes an ultrasound image display method and apparatus, a storage medium, and an electronic device. The method includes acquiring, by a device, an input signal by performing detection on a to-be-detected object, the input signal comprising a three-dimensional (3D) radio-frequency (RF) signal. The device includes a memory storing instructions and a processor in communication with the memory. The method also includes performing, by the device, a modulus calculation on the 3D RF signal to obtain envelope information in a 3D ultrasound image, the modulus calculation being at least used for directly acquiring a 3D amplitude of the 3D RF signal; and displaying, by the device, the envelope information in the 3D ultrasound image, the envelope information being at least used for indicating the to-be-detected object.

14 Claims, 16 Drawing Sheets

(51) Int. Cl.
*G06F 17/14* (2006.01)
*A61B 8/00* (2006.01)

(56) References Cited

FOREIGN PATENT DOCUMENTS

CN 103512960 A 1/2014
JP 2005087237 A 4/2005

OTHER PUBLICATIONS

International Search Report with English translation and Written Opinion regarding PCT/CN2019/082216 dated Jul. 8, 2019, 8 pages.
Extended European Search Report regarding EP19808389 dated May 21, 2021.
Wang et al., "3-D biquaternionic analytic signal and application to envelope detection in 3-D ultrasound imaging," 2012 International Conference on 3D Imaging (IC3D), IEEE, Lyon, France, Dec. 3, 2012, pp. 1-8.
Snopek, "The n-D analytic 2-5, 7-10 signals and Fourier spectra in complex and hypercomplex domains," Telecommunications and Signal Processing (TSP), 2011, 34th International Conference IEEE, Aug. 18, 2018, pp. 423-427.
Bulow et al., "Hypercomplex Signals—A Novel Extension of the Analytic Signal to the Multidimensional Case," IEEE Transactions on Signal Processing, IEEE Service Center, New York, NY, Nov. 1, 2001, pp. 2844-2852.

* cited by examiner

US 11,486,862 B2

ULTRASOUND IMAGE DISPLAY METHOD AND APPARATUS, STORAGE MEDIUM, AND ELECTRONIC DEVICE

RELATED APPLICATION

This application is a continuation application of PCT Patent Application No. PCT/CN2019/082216, filed on Apr. 11, 2019, which claims priority to Chinese Patent Application No. 201810508663.2, filed with the National Intellectual Property Administration, P.R. China on May 24, 2018, both of which are incorporated herein by reference in their entireties.

FIELD OF THE TECHNOLOGY

This application relates to the field of computers, and specifically, to display of an ultrasound image.

BACKGROUND OF THE DISCLOSURE

Envelope detection is an important step of reconstruction of a brightness-mode ultrasound image (B-mode ultrasound image). A basic process of the reconstruction of the B-mode ultrasound image includes: acquiring a high-frequency radio frequency (RF) signal from an ultrasound probe, the original RF signal being a one-dimensional signal along a direction of the ultrasound probe; then performing the Hilbert transform on the one-dimensional signal to construct a one-dimensional analytic signal, an amplitude value of the one-dimensional analytic signal calculated being a one-dimensional envelope signal; and splicing a plurality of one-dimensional envelope signals into a two-dimensional signal according to a location of the probe, to acquire a two-dimensional envelope image and acquire a two-dimensional B-mode ultrasound image after some post-processing. At present, a three-dimensional (3D) B-mode ultrasound image is mostly acquired after some post-processing is performed a 3D envelope image that is obtained through splicing based on one-dimensional envelope signals.

SUMMARY

Embodiments of this application provide an ultrasound image display method and apparatus, a storage medium and an electronic device, to improve the accuracy of a three-dimensional (3D) B-mode ultrasound image.

The present disclosure describes a method for displaying an ultrasound image. The method includes acquiring, by a device, an input signal by performing detection on a to-be-detected object, the input signal comprising a three-dimensional (3D) radio-frequency (RF) signal. The device includes a memory storing instructions and a processor in communication with the memory. The method also includes performing, by the device, a modulus calculation on the 3D RF signal to obtain envelope information in a 3D ultrasound image, the modulus calculation being at least used for directly acquiring a 3D amplitude of the 3D RF signal; and displaying, by the device, the envelope information in the 3D ultrasound image, the envelope information being at least used for indicating the to-be-detected object.

The present disclosure describes an apparatus for displaying an ultrasound image. The apparatus includes a memory storing instructions; and a processor in communication with the memory. When the processor executes the instructions, the processor is configured to cause the apparatus to acquire an input signal by performing detection on a to-be-detected object, the input signal comprising a three-dimensional (3D) radio-frequency (RF) signal, perform a modulus calculation on the 3D RF signal to obtain envelope information in a 3D ultrasound image, the modulus calculation being at least used for directly acquiring a 3D amplitude of the 3D RF signal, and display the envelope information in the 3D ultrasound image, the envelope information being at least used for indicating the to-be-detected object.

The present disclosure describes a non-transitory computer readable storage medium storing computer readable instructions. The computer readable instructions, when executed by a processor, are configured to cause the processor to perform acquiring an input signal by performing detection on a to-be-detected object, the input signal comprising a three-dimensional (3D) radio-frequency (RF) signal; performing a modulus calculation on the 3D RF signal to obtain envelope information in a 3D ultrasound image, the modulus calculation being at least used for directly acquiring a 3D amplitude of the 3D RF signal; and displaying the envelope information in the 3D ultrasound image, the envelope information being at least used for indicating the to-be-detected object.

According to another aspect of the embodiments of this application, an electronic device is further provided, including a memory and a processor, the memory storing a computer program, and the processor being configured to perform any ultrasound image display method in the embodiments of this application through the computer program.

BRIEF DESCRIPTION OF THE DRAWINGS

The accompanying drawings described herein are used for providing a further understanding of this application, and form a part of this application. Exemplary embodiments of this application and descriptions thereof are used for explaining this application, and do not constitute any inappropriate limitation to this application. In the accompanying drawings.

DESCRIPTION OF EMBODIMENTS

Figure 1:
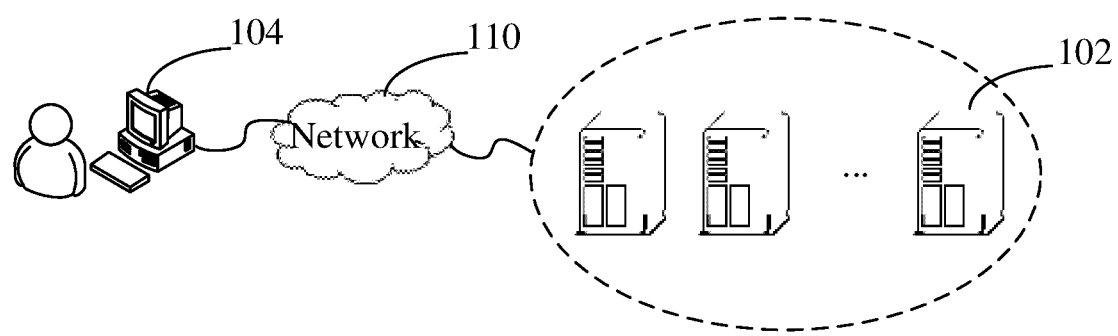
FIG. 1 is a schematic diagram of a hardware environment of an ultrasound image display method according to an embodiment of this application.

To make solutions of this application more comprehensible for a person skilled in the art, the following clearly and completely describes the technical solutions in the embodiments of this application with reference to the accompanying drawings in the embodiments of this application. Apparently, the described embodiments are merely a part rather than all of the embodiments of this application. All other embodiments obtained by a person of ordinary skill in the art based on the embodiments of this application without creative efforts shall fall within the protection scope of this application.

The terms such as "first" and "second" in the specification, claims, and accompanying drawings of this application are intended to distinguish between similar objects rather than describe a particular sequence or a chronological order. It is to be understood that the data termed in such a way are interchangeable in proper circumstances so that the embodiments of this application described herein can be implemented in orders except the order illustrated or described herein. In addition, the terms "include", "comprise" and any other variants are intended to cover the non-exclusive inclusion. For example, a process, method, system, product, or device that includes a series of steps or units is not necessarily limited to those expressly listed steps or units, but may include other steps or units not expressly listed or inherent to such a process, method, product, or device.

Throughout the specification and claims, terms may have nuanced meanings suggested or implied in context beyond an explicitly stated meaning. Likewise, the phrase "in one embodiment" or "in one implementation" as used herein does not necessarily refer to the same embodiment or implementation and the phrase "in another embodiment" or "in another implementation" as used herein does not necessarily refer to a different embodiment or implementation. It is intended, for example, that claimed subject matter includes combinations of exemplary embodiments or implementations in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

According to an aspect of the embodiments of this application, an ultrasound image display method is provided.

Optionally, in this embodiment, the ultrasound image display method may be applied to a hardware environment composed of a server 102 and a detection device 104 shown in FIG. 1. As shown in FIG. 1, the server 102 is connected to the detection device 104 by a network 110. The network 110 includes, but is not limited to, a wide area network, a metropolitan area network or a local area network. The detection device 104 may include, but is not limited to, an ultrasound device.

Optionally, the ultrasound image display method in this embodiment of this application may be performed by the detection device 104 and a display device together. The specific execution process may be described as: acquiring, by the detection device, an input signal obtained by performing detection on a to-be-detected object by the detection device, the input signal being a three-dimensional (3D) radio-frequency (RF) signal; performing a one-time modulus value calculation on the 3D RF signal to obtain envelope information in a 3D ultrasound image, the one-time modulus value calculation being at least used for directly acquiring a 3D amplitude of the 3D RF signal; generating, by the detection device, the 3D ultrasound image according to the envelope information and sending the 3D ultrasound image to the display device; and displaying the envelope information in the 3D ultrasound image on the display device, the envelope information being used for indicating the to-be-detected object.

Optionally, the detection device and the display device may form an integral structure. For example, the detection device 104 shown in FIG. 1 is the integral structure composed of the detection device and the display device. Alternatively, the detection device and the display device may be separate components. The detection device is configured to generate the 3D ultrasound image and the display device is configured to display the 3D ultrasound image.

The following provides a detailed description about the ultrasound image display method in this embodiment of this application.

Figure 2:
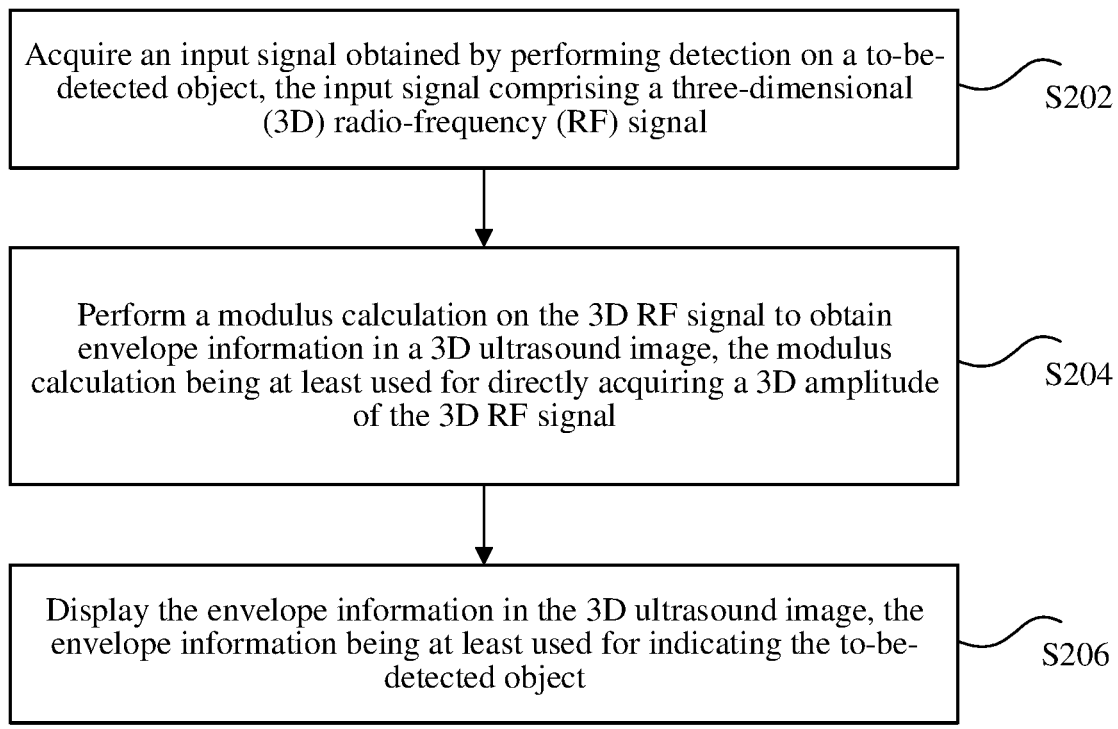
FIG. 2 is a flowchart of an optional ultrasound image display method according to an embodiment of this application.

FIG. 2 is a flowchart of an optional ultrasound image display method according to an embodiment of this application. As shown in FIG. 2, the method may include the following steps:

S202. Acquire an input signal obtained by performing detection on a to-be-detected object, the input signal comprising a three-dimensional (3D) radio-frequency (RF) signal.

S204. Perform a modulus calculation on the 3D RF signal to obtain envelope information in a 3D ultrasound image, the modulus calculation being at least used for directly acquiring a 3D amplitude of the 3D RF signal.

In one implementation, the modulus calculation on the 3D RF signal may include a one-time modulus value calculation on the 3D RF signal to obtain the envelope information in the 3D ultrasound image.

S206. Display the envelope information in the 3D ultrasound image, the envelope information being at least used for indicating the to-be-detected object.

Through the foregoing S202 to S206, by acquiring the input signal obtained by performing the detection on the to-be-detected object by the detection device, the input signal being the 3D RF signal; performing the modulus calculation on the 3D RF signal to obtain the envelope information in the 3D ultrasound image, the modulus calculation being at least used for directly acquiring the 3D amplitude of the 3D RF signal; and displaying the envelope information in the 3D ultrasound image on the display device, the envelope information being used for indicating the to-be-detected object, the to-be-detected object is accurately displayed in the 3D ultrasound image, to achieve a technical effect of improving the accuracy of the 3D ultrasound image, thereby solving the technical problem that the 3D B-mode ultrasound image reconstructed in the related art has a reconstruction error that reduces the accuracy of the 3D B-mode ultrasound image.

In the technical solution provided in S202, the detection device may include, but is not limited to, an ultrasound device. The detection device may be configured to detect the to-be-detected object, a type of the to-be-detected object being not specifically limited in this embodiment of this application. For example, the to-be-detected object may be a human organ (for example, the kidney or the liver). When the detection device detects the to-be-detected object, the detection device may send a detection signal. A signal obtained after the detection signal is reflected by the to-be-detected object is an input signal, where the input signal may be a real signal and/or the input signal may be a high-frequency 3D RF signal.

In the technical solution provided in S204, after the input signal is acquired, in this embodiment of this application, the modulus calculation may be performed on the input signal, that is, the modulus calculation is performed on the 3D RF signal, to obtain the envelope information in the 3D ultrasound image, where the envelope information in the 3D ultrasound image may be used for indicating the to-be-detected object. The modulus calculation may at least be used for directly acquiring the 3D amplitude of the 3D RF signal, where the envelope information may include the 3D amplitude of the 3D RF signal. In this embodiment of this application, by performing the modulus calculation on the 3D RF signal, the envelope information in the 3D ultrasound image is obtained. Compared with obtaining the 3D ultrasound image by splicing one-dimensional envelope information, this embodiment of this application may make the brightness of the to-be-detected object indicated by the envelope information in the 3D ultrasound image be greater than the brightness of the to-be-detected object in a one-dimensional ultrasound image or a two-dimensional ultrasound image, to clearly display the to-be-detected object in the 3D ultrasound image, thereby improving the accuracy of the 3D ultrasound image.

The following provides a detailed description about a specific process of performing the modulus calculation on the 3D RF signal to obtain the envelope information in the 3D ultrasound image:

Optionally, S204 of performing the modulus calculation on the 3D RF signal may include the following S2042 and S2044:

S2042. Acquire a first hypercomplex signal corresponding to the 3D RF signal, the first hypercomplex signal being a sum of 8 components, and each component being represented by modulus values and angles of a plurality of analytic signals corresponding to the input signal.

S2044. Acquire a modulus value of the first hypercomplex signal, the modulus value of the first hypercomplex signal being used for representing the 3D amplitude of the 3D RF signal, and envelope information including the modulus value of the first hypercomplex signal.

For S2042, optionally, the acquiring the first hypercomplex signal corresponding to the input signal may include: acquiring a second hypercomplex signal corresponding to the input signal, the second hypercomplex signal including 8 components, and each component being represented by the Hilbert transform of the input signal; acquiring a correspondence between the components represented by the Hilbert transform and the modulus values and angles of the plurality of analytic signals; and transforming the second hypercomplex signal into the first hypercomplex signal according to the correspondence.

Optionally, the input signal of the 3D RF signal may be defined as f(x, y, z) herein, and a hypercomplex signal $\psi_{cas}$ (x, y, z) of f(x, y, z) is defined as formula (3):

$$\psi_{cas}(x, y, z) = f(x, y, z) \star\star\star \left\{ \left[\delta(x) + \frac{e_1}{\pi x}\right]\left[\delta(y) + \frac{e_2}{\pi y}\right]\left[\delta(z) + \frac{e_3}{\pi z}\right] \right\}. \quad (3)$$

The hypercomplex signal $\psi_{cas}$(x, y, z) uses 3 bases of complex units: $e_1$, $e_2$, and $e_3$, to define an imaginary unit. The theoretical foundation thereof is derived from the definition of a biquaternion. The following explains related contents:

When it is defined that $e_1=e_2=e_3=i$, they are a conventional imaginary unit i shown in formula (1).

Conventional one-dimensional envelope detection is implemented by using a one-dimensional analytic signal. For a one-dimensional RF signal f(x), the one-dimensional Hilbert transform H{f(x)}, and they are respectively used as a real part and an imaginary part to form a complex signal, that is, the one-dimensional analytic signal $f_A(x)$, as shown in formula (1):

$$f_A(x) = f(x) + iH\{f(x)\}, x \in \mathbb{R} \quad (1)$$

i is the complex unit and x belongs to a real number R. An amplitude value of the one-dimensional high-frequency signal is shown in formula (2):

$$|f_A(x)| = \sqrt{f(x)^2 + (H\{f(x)\})^2} \quad (2)$$

When e1, e2, and e3 are different from each other, they can generate 8 different imaginary units ($2^3=8$). The definition is shown in formula (4):

$$[1, i=c_2c_3, j=e_3e_1, k=e_1e_2, \epsilon=-e_1e_2e_3, \epsilon i=e_1, \epsilon j=e_2, \epsilon k=e_3] \quad (4)$$

where 1 represents the real part, $\epsilon^2=1$, and $e_1^2=e_2^2=e_3^2=-1$.

Figure 3:
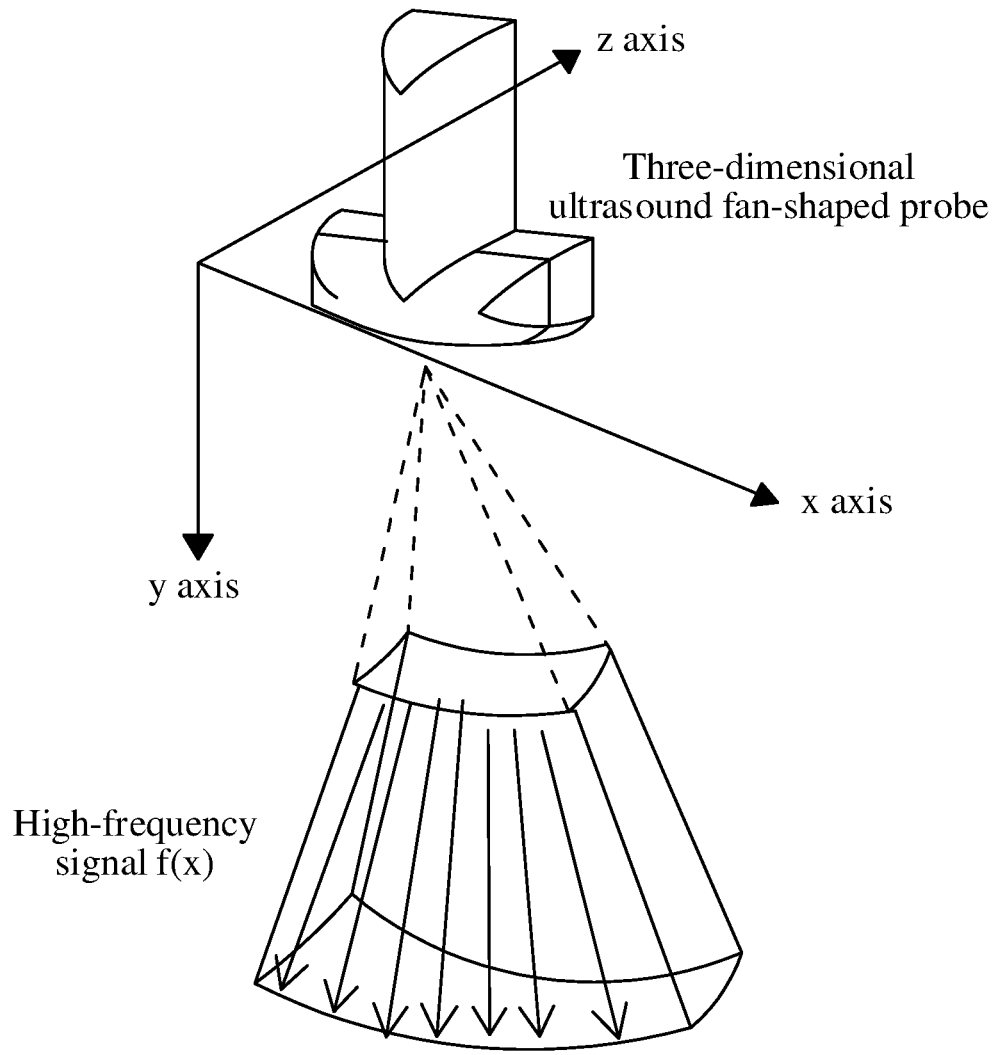
FIG. 3 is a schematic diagram of forming a plane by splicing envelopes of one-dimensional signals in the related art.

In formula (3), *** represents a 3D convolution calculation. δ(x), δ(y), and δ(z) are Dirac delta functions. For the 3D RF signal, the x axis, the y axis and the z axis herein may respectively correspond to physical interpretations of the x axis, the y axis and the z axis in FIG. 3. FIG. 3 is a schematic diagram of sending a RF signal by a 3D ultrasound fan-shaped probe. The high-frequency signal f(x) represents a one-dimensional RF signal sent by the ultrasound probe. A plurality of one-dimensional RF signals form one plane and a plurality of planes form one piece of 3D RF volume data.

Formula (3) is further spread out and calculated to obtain formula (5):

$$\psi_{cas}(x, y, z) = \qquad (5)$$
$$f(x, y, z) \star\star\star \left\{ \left[\delta(x) + \frac{e_1}{\pi x}\right]\left[\delta(y) + \frac{e_2}{\pi y}\right]\left[\delta(z) + \frac{e_3}{\pi z}\right] \right\} = f(x, y, z)$$
$$\star\star\star \left\{ \delta(x)\delta(y)\delta(z) + \delta(x)\delta(y)\frac{e_3}{\pi z} + \delta(x)\frac{e_2}{\pi y}\delta(z) + \delta(x)\frac{e_2}{\pi y}\frac{e_3}{\pi z} + \right.$$
$$\left. \frac{e_1}{\pi x}\delta(y)\delta(z) + \frac{e_1}{\pi x}\delta(y)\frac{e_3}{\pi z} + \frac{e_1}{\pi x}\frac{e_2}{\pi y}\delta(z) + \frac{e_1}{\pi x}\frac{e_2}{\pi y}\frac{e_3}{\pi z} \right\},$$

The convolution calculation in formula (5) is spread out, and the following 8 convolution calculations may be seen (see formula (6)). In addition, according to formula (4), an imaginary unit of each convolution in formula (6) may be calculated, as shown in formula (6):

$$f(x, y, z) \star\star\star [\delta(x)\delta(y)\delta(z)] = f(x, y, z), \qquad (6)$$
$$f(x, y, z) \star\star\star \left[\delta(x)\delta(y)\frac{e_3}{\pi z}\right] = e_3 H_z\{f\} = \epsilon k H_z\{f\},$$
$$f(x, y, z) \star\star\star \left[\delta(x)\frac{e_2}{\pi y}\delta(z)\right] = e_2 H_y\{f\} = \epsilon j H_y\{f\},$$
$$f(x, y, z) \star\star\star \left[\frac{e_1}{\pi x}\delta(y)\delta(z)\right] = e_1 H_x\{f\} = \epsilon i H_x\{f\},$$
$$f(x, y, z) \star\star\star \left[\delta(x)\frac{e_2}{\pi y}\frac{e_3}{\pi z}\right] = e_2 e_3 H_{yz}\{f\} = i H_{yz}\{f\},$$
$$f(x, y, z) \star\star\star \left[\frac{e_1}{\pi x}\delta(y)\frac{e_3}{\pi z}\right] = e_1 e_3 H_{xz}\{f\} = -e_3 e_1 H_{xz}\{f\} = -j H_{xz}\{f\},$$
$$f(x, y, z) \star\star\star \left[\frac{e_1}{\pi x}\frac{e_2}{\pi y}\delta(z)\right] = e_1 e_2 H_{xy}\{f\} = k H_{xy}\{f\},$$
$$f(x, y, z) \star\star\star \left[\frac{e_1}{\pi x}\frac{e_2}{\pi y}\frac{e_3}{\pi z}\right] = e_1 e_2 e_3 H\{f\} = -\epsilon H\{f\}.$$

In formula (6), H{f} represents the Hilbert transform of signal f(x, y, z). $H_z\{f\}$ represents the Hilbert transform of signal f(x, y, z) in the z direction, $H_y\{f\}$ represents the Hilbert transform of signal f(x, y, z) in the y direction, $H_x\{f\}$ represents the Hilbert transform of signal f(x, y, z) in the x direction, $H_{yz}\{f\}$ represents the Hilbert transform of signal f(x, y, z) in the y direction and the z direction, $H_{xz}\{f\}$ represents the Hilbert transform of signal f(x, y, z) in the x direction and the z direction, and $H_{xy}\{f\}$ represents the Hilbert transform of signal f(x, y, z) in the x direction and the y direction.

If a result of formula (6) is substituted into formula (5), a hypercomplex signal $\psi_{cas}$ (x, y, z) may be written as shown in formula (7):

$$\psi_{cas}(x, y, z) = f + iH_{yz}\{f\} + j(-H_{xz}\{f\}) + \qquad (7)$$
$$kH_{xy}\{f\} + \epsilon(-H\{f\}) + \epsilon i H_x\{f\} + \epsilon j H_y\{f\} + \epsilon k H_z\{f\}$$

The hypercomplex signal in formula (7) is the second hypercomplex signal in this embodiment of this application.

In conclusion, the second hypercomplex signal corresponding to the input signal f(x, y, z) of the 3D RF signal is shown in formula (7). Each component of the hypercomplex signal is represented by the Hilbert transform of the input signal.

Formula (7) is a theoretical value. Next, each component needs to be calculated from the perspective of engineering, and then the amplitude value (theoretical value) of the hypercomplex signal is calculated, thereby acquiring the amplitude value (theoretical value) of the hypercomplex signal from the perspective of engineering.

The foregoing content defines the hypercomplex signal in a form of convolution, and defines the imaginary unit of the hypercomplex signal by using three bases of the biquaternion. The beneficial effect is that the form of definition is a macroscopic form of a conventional complex number and a quaternion, and may process 3D data and express the conventional complex number (one real part and one imaginary part) and the quaternion (one real part and three imaginary parts) in a downward compatible manner.

A method for indirectly calculating the Hilbert transform in each component of the hypercomplex signal is needed to acquire a mathematical expression, of a result of formula (7), that can be implemented in engineering.

Because it is very difficult to directly calculate the Hilbert transform theoretically, a method for indirectly calculating the Hilbert transform is described herein. The method may be implemented in engineering but not in a theoretical formula.

Engineering implementation means that: it may be implemented by using a common programming language and an open code library.

For the input signal f(x, y, z) of the 3D RF signal, a calculated single-orthant analytic signal of f(x, y, z) is a signal obtained by performing inverse Fourier transform on a single orthant of a 3D Fourier spectrum of a real signal f(x, y, z). The signal may be calculated by using a Fourier transform function of a general programming language.

Figure 4:
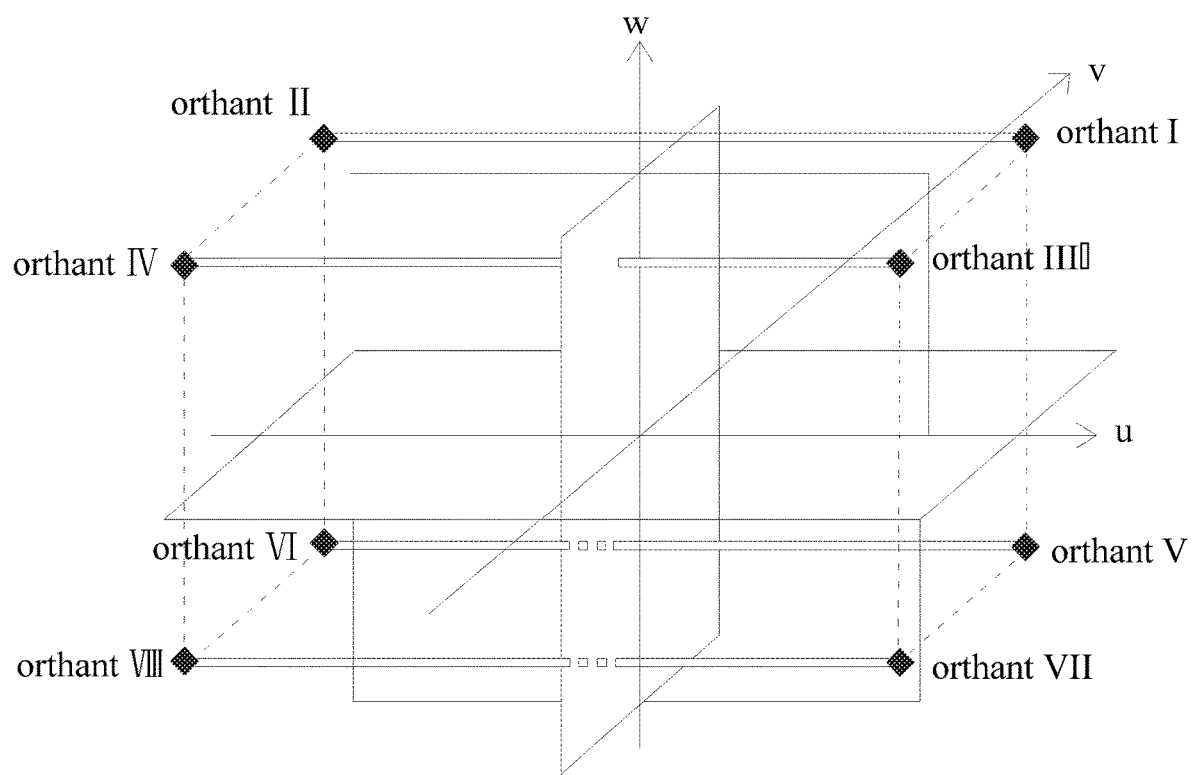
FIG. 4 is a schematic diagram of 8 orthants in a 3D frequency domain according to an embodiment of this application.

One 3D real signal is first transformed from a 3D real number domain to a 3D frequency domain through the Fourier transform. There are 8 orthants in the 3D frequency domain, as shown in FIG. 4. In the 3D frequency domain, half of the spectrum includes all information about the whole original signal. Therefore, in the 8 orthants of the 3D frequency domain, four adjacent orthants may be selected to include all information about the input signal. FIG. 4 shows the eight orthants in the 3D frequency domain. It can be seen that, orthant I, orthant III, orthant V, and orthant VII are four adjacent orthants.

The eight orthants in the 3D frequency domain are in FIG. 4, where u, v, and w are 3 dimensions of the frequency domain.

The following describes a calculation process of four single-orthant analytic signals, as shown in formula (8) to formula (11):

$$\psi_1(x, y, z) = f(x, y, z) \star\star\star \left\{ \left[\delta(x) + \frac{i}{\pi x}\right]\left[\delta(y) + \frac{i}{\pi y}\right]\left[\delta(z) + \frac{i}{\pi z}\right] \right\} = \qquad (8)$$
$$(f - H_{xy}\{f\} - H_{xz}\{f\} - H_{yz}\{f\}) +$$
$$i(H_x\{f\} + H_y\{f\} + H_z\{f\} - H\{f\}) =$$
$$a_1 e^{i\varphi_1} = a_1 \cos\varphi_1 + i a_1 \sin\varphi_1,$$

$$\psi_3(x, y, z) = f(x, y, z) \star\star\star \left\{ \left[\delta(x) + \frac{i}{\pi x}\right]\left[\delta(y) - \frac{i}{\pi y}\right]\left[\delta(z) + \frac{i}{\pi z}\right] \right\} = \qquad (9)$$
$$(f + H_{xy}\{f\} - H_{xz}\{f\} + H_{yz}\{f\}) +$$
$$i(H_x\{f\} - H_y\{f\} + H_z\{f\} + H\{f\}) =$$
$$a_3 e^{i\varphi_3} = a_3 \cos\varphi_3 + i a_3 \sin\varphi_3,$$

$$\psi_5(x, y, z) = f(x, y, z) \star\star\star \left\{ \left[\delta(x) + \frac{i}{\pi x}\right]\left[\delta(y) + \frac{i}{\pi y}\right]\left[\delta(z) - \frac{i}{\pi z}\right] \right\} = \quad (10)$$
$$(f - H_{xy}\{f\} + H_{xz}\{f\} + H_{yz}\{f\}) +$$
$$i(H_x\{f\} + H_y\{f\} - H_z\{f\} + H\{f\}) =$$
$$a_5 e^{i\varphi_5} = a_5 \cos\varphi_5 + ia_5 \sin\varphi_5,$$

$$\psi_7(x, y, z) = f(x, y, z) \star\star\star \left\{ \left[\delta(x) + \frac{i}{\pi x}\right]\left[\delta(y) - \frac{i}{\pi y}\right]\left[\delta(z) - \frac{i}{\pi z}\right] \right\} = \quad (11)$$
$$(f + H_{xy}\{f\} + H_{xz}\{f\} - H_{yz}\{f\}) +$$
$$i(H_x\{f\} - H_y\{f\} - H_z\{f\} - H\{f\}) =$$
$$a_7 e^{i\varphi_7} = a_7 \cos\varphi_7 + ia_7 \sin\varphi_7.$$

$\psi_1(x, y, z)$, $\psi_3(x, y, z)$, $\psi_5(x, y, z)$, and $\omega_7(x, y, z)$ represent single-orthant analytic signals respectively acquired from orthant I, orthant III, orthant V, and orthant VII of the frequency domain in FIG. 4. The difference between the signal and the definition in formula (3) is that: the definition uses the unique imaginary unit i, that is the most conventional definition of the complex number (a complex number including one real part and one imaginary part). Similar to the calculation method of formula (6), a 3D convolution of formula (8) to formula (11) has 8 components. The 8 components may each be represented by the Hilbert transform of the input signal f(x, y, z), which form real parts and imaginary parts of the single-orthant analytic signals.

Further, the foregoing formulas also define modulus values and angles of the single-orthant analytic signals (that is, a form of polar coordinates of a complex number $\psi_1(x, y, z)$). For example, in formula (8), $\alpha_1(x, y, z)$ represents the modulus value in the form of the polar coordinates of the complex number $\psi_1(x, y, z)$ ($\alpha_1$ herein may also be referred to as an amplitude value). In formula (8), $\alpha_1(x, y, z)$ is shortened to $\alpha_1$. $\varphi_1(x, y, z)$ represents the angle in the form of the polar coordinates of the complex number $\psi_1(x, y, z)$ ($\varphi_1$ may also be referred to as the phase herein). Similarly, in formula (8), $\varphi_1(x, y, z)$ is shortened to $\varphi_1$. A specific calculation method thereof is shown in formula (12):

$$a_1 = \sqrt{\frac{(f - H_{xy}\{f\} - H_{xz}\{f\} - H_{yz}\{f\})^2 +}{(H_x\{f\} + H_y\{f\} + H_z\{f\} - H\{f\})^2}} \quad (12)$$

$$\varphi_1 = \arctan\left(\frac{H_x\{f\} + H_y\{f\} + H_z\{f\} - H\{f\}}{f - H_{xy}\{f\} - H_{xz}\{f\} - H_{yz}\{f\}}\right)$$

The relationship between the modulus value $\alpha_1$, the angle $\varphi_1$ and the Hilbert transform may be obtained by formula (8), as shown in formula (13):

$$\alpha_1 \cos\varphi_1 = f - H_{xy}\{f\} - H_{xz}\{f\} - H_{yz}\{f\}$$

$$\alpha_1 \sin\varphi_1 = H_x\{f\} + H_y\{f\} + H_z\{f\} - H\{f\} \quad (13)$$

Similarly, the correspondence between the modulus values, the angles and the Hilbert transform of the other three single-orthant analytic signals may be obtained from formula (9) to formula (11), as shown in formula (14):

$f = \frac{1}{4}(\alpha_1 \cos \varphi_1 + \alpha_3 \cos \varphi_3 + \alpha_5 \cos \varphi_5 + \alpha_7 \cos \varphi_7)$, $H_{yz}\{f\} = \frac{1}{4}(-\alpha_1 \cos \varphi_1 + \alpha_3 \cos \varphi_3 + \alpha_5 \cos \varphi_5 - \alpha_7 \cos \varphi_7)$, $-H_{xz}\{f\} = \frac{1}{4}(\alpha_1 \cos \varphi_1 + \alpha_3 \cos \varphi_3 - \alpha_5 \cos \varphi_5 - \alpha_7 \cos \varphi_7)$, $H_{xy}\{f\} = \frac{1}{4}(-\alpha_1 \cos \varphi_1 + \alpha_3 \cos \varphi_3 - \alpha_5 \cos \varphi_5 + \alpha_7 \cos \varphi_7)$, $-H\{f\} = \frac{1}{4}(\alpha_1 \sin \varphi_1 - \alpha_3 \sin \varphi_3 - \alpha_5 \sin \varphi_5 + \alpha_7 \sin \varphi_7)$, $H_x\{f\} = \frac{1}{4}(\alpha_1 \sin \varphi_1 + \alpha_3 \sin \varphi_3 + \alpha_5 \sin \varphi_5 + \alpha_7 \sin \varphi_7)$, $H_y\{f\} = \frac{1}{4}(\alpha_1 \sin \varphi_1 - \alpha_3 \sin \varphi_3 + \alpha_5 \sin \varphi_5 - \alpha_7 \sin \varphi_7)$, $H_z\{f\} = \frac{1}{4}(\alpha_1 \sin \varphi_1 + \alpha_3 \sin \varphi_3 - \alpha_5 \sin \varphi_5 - \alpha_7 \sin \varphi_7)$, (14)

Formula (14) may be used for representing a correspondence between the components represented by the Hilbert transform and the modulus value and angle of the analytic signal in this embodiment of this application.

Formula (14) uses the modulus value and angle of the analytic signal of the input signal to represent the Hilbert transform. It is relatively difficult to obtain, through a calculation, the left part of formula (14) in engineering, while the right part of formula (14) may be obtained through a calculation of a library function of the Fourier transform of the conventional programming language.

By substituting the result of formula (14) into formula (7), the hypercomplex signal $\psi_{cas}(x, y, z)$ defined in mathematical theory is calculated by the library function of the Fourier transform of the conventional programming language, which is the expression shown in formula (15):

$$\psi_{cas} = \frac{1}{4}[(a_1\cos\varphi_1 + a_3\cos\varphi_3 + a_5\cos\varphi_5 + a_7\cos\varphi_7) + \quad (15)$$
$$i(-a_1\cos\varphi_1 + a_3\cos\varphi_3 + a_5\cos\varphi_5 - a_7\cos\varphi_7) +$$
$$j(a_1\cos\varphi_1 + a_3\cos\varphi_3 - a_5\cos\varphi_5 - a_7\cos\varphi_7) +$$
$$k(-a_1\cos\varphi_1 + a_3\cos\varphi_3 - a_5\cos\varphi_5 + a_7\cos\varphi_7) +$$
$$\epsilon(a_1\sin\varphi_1 - a_3\sin\varphi_3 - a_5\sin\varphi_5 + a_7\sin\varphi_7) +$$
$$\epsilon i(a_1\sin\varphi_1 + a_3\sin\varphi_3 + a_5\sin\varphi_5 + a_7\sin\varphi_7) +$$
$$\epsilon j(a_1\sin\varphi_1 - a_3\sin\varphi_3 + a_5\sin\varphi_5 - a_7\sin\varphi_7) +$$
$$\epsilon k(a_1\sin\varphi_1 + a_3\sin\varphi_3 - a_5\sin\varphi_5 - a_7\sin\varphi_7)].$$

The hypercomplex signal in formula (15) is the first hypercomplex signal in this embodiment of this application.

In conclusion, the foregoing content theoretically converts the content of the hypercomplex signal $\psi_{cas}(x, y, z)$ into an expression in another form, aiming to acquire an expression of the hypercomplex signal $\psi_{cas}(x, y, z)$ that can be implemented in engineering, as shown in formula (15).

After acquiring the first hypercomplex signal shown in formula (15), the modulus value of the first hypercomplex signal may be calculated. The specific process of calculating the modulus value $|\psi_{cas}(x, y, z)|$ of the hypercomplex signal may be described as follows:

Properties of several biquaternions need to be used when the modulus value is calculated:

Biquaternion property 1: multiplication of the biquaternion;

for a biquaternion A, the expression thereof may be shown in formula (16):

$$A = p + \epsilon q \quad (16)$$
$$= (p_0 + ip_1 + jp_2 + kp_3) + \epsilon(q_0 + iq_1 + jq_2 + kq_3)$$
$$= p_0 + ip_1 + jp_2 + kp_3 + \epsilon q_0 + \epsilon iq_1 + \epsilon jq_2 + \epsilon kq_3$$

Both p and q are quaternions. It is defined that another biquaternion B=p'±ϵq', and the product of the two biquaternions is shown in formula (17):

$$AB=(p+\epsilon q)(p'+\epsilon q')=(pp'+qq')+\epsilon(pq'+qp') \quad (17)$$

where the quaternion product theory of the quaternions p, q, p', and q' is not described herein.

Biquaternion property 2: conjugate of the biquaternion;

conjugate of the biquaternion A may be defined as Ac, as shown in formula (18):

$$A_c = p_c + \epsilon q_c \quad (18)$$
$$= (p_0 - ip_1 - jp_2 - kp_3) + \epsilon(q_0 - iq_1 - jq_2 - kq_3)$$
$$= p_0 - ip_1 - jp_2 - kp_3 + \epsilon q_0 - \epsilon iq_1 - \epsilon jq_2 - \epsilon kq_3$$

$p_c$ is conjugate of quaternion p.

In order to calculate the modulus value $|\psi_{cas}(x, y, z)|$ of the hypercomplex signal, formulas (16) to (19) need to be first used to calculate the product of $\psi_{cas}(x, y, z)$ and the conjugate thereof, that is, $\psi_{cas}(\psi_{cas})_c$, as shown in formula (19):

$$\psi_{cas}(\varphi_{cas})_c = \frac{a_1^2 + a_3^2 + a_5^2 + a_7^2}{4} + i(0) + j(0) + k(0) + \quad (19)$$
$$\epsilon \frac{a_1 a_3 \sin(\varphi_1 - \varphi_3) - a_5 a_7 \sin(\varphi_5 - \varphi_7)}{2} + \epsilon i(0) + \epsilon j(0) + \epsilon k(0) =$$
$$\frac{a_1^2 + a_3^2 + a_5^2 + a_7^2}{4} + \epsilon \frac{a_1 a_3 \sin(\varphi_1 - \varphi_3) - a_5 a_7 \sin(\varphi_5 - \varphi_7)}{2},$$

It can be seen from formula (19) that, a result of $\psi_{cas}(\psi_{cas})_c$ only includes two parts, where one part is a real part, that is, $$\frac{a_1^2 + a_3^2 + a_5^2 + a_7^2}{4},$$

the other part is a part that takes ϵ as an imaginary unit, that is, $$\epsilon \frac{a_1 a_3 \sin(\varphi_1 - \varphi_3) - a_5 a_7 \sin(\varphi_5 - \varphi_7)}{2},$$

and actually, the part is referred to as a "pseudo real" part of a biquaternion. Other imaginary parts are all 0. The result is greatly helpful in calculating the modulus value $|\psi_{cas}(x, y, z)|$. The following describes a process of calculating the modulus value $|\psi_{cas}(x, y, z)|$.

First, a polar coordinate form of a hypercomplex signal $\psi_{cas}(x, y, z)$:

$$\psi_{cas}=|\psi_{cas}|e^{\epsilon\phi a},$$

$|\psi_{cas}|$ is a modulus value, a is a unit biquaternion (that has a property: a product of conjugate and itself is 1, namely, $a(a_c)=1$), and ϕ is an angle of the biquaternion. As shown in formula (20):

$$\psi_{cas}(\psi_{cas})_c=|\psi_{cas}|^2 e^{2\epsilon\phi}=|\psi_{cas}|^2[ch(2\phi)+\epsilon sh(2\phi)], \quad (20)$$

ch( ) and sh( ) are a hyperbolic cosine function and a hyperbolic sine function respectively. The specific derivation process of the formula is shown as follows:

$$e^{2\epsilon\phi} = 1 + 2\epsilon\phi + \frac{(2\epsilon\phi)^2}{2!} + \frac{(2\epsilon\phi)^3}{3!} + \ldots + \frac{(2\epsilon\phi)^{2r}}{(2r)!} + + \frac{(2\epsilon\phi)^{2r+1}}{(2r+1)!} + \ldots$$
$$= \left[1 + \frac{(2\epsilon\phi)^2}{2!} + \frac{(2\epsilon\phi)^4}{4!} + \ldots + \frac{(2\epsilon\phi)^{2r}}{(2r)!} + \ldots\right] +$$
$$\left[2\epsilon\phi + \frac{(2\epsilon\phi)^3}{3!} + \frac{(2\epsilon\phi)^5}{5!} + \ldots + \frac{(2\epsilon\phi)^{2r+1}}{(2r+1)!} + \ldots\right]$$
$$= \left[1 + \frac{(2\epsilon\phi)^2}{2!} + \frac{(2\epsilon\phi)^4}{4!} + \ldots + \frac{(2\epsilon\phi)^{2r}}{(2r)!} + \ldots\right] +$$
$$\epsilon\left[2\phi + \frac{(2\phi)^3}{3!} + \frac{(2\phi)^5}{5!} + \ldots + \frac{(2\phi)^{2r+1}}{(2r+1)!} + \ldots\right]$$
$$= ch(2\phi) + \epsilon sh(2\phi),$$

where r represents a positive complex number.

In order to simplify the calculation, two symbols M and N may be used to represent formula (20):

$$\psi_{cas}(\psi_{cas})_c=M+\epsilon N$$

M represents real parts in formula (19) and formula (20), and N represents "pseudo real" parts in formula (19) and formula (20). The following may be obtained:

$$M^2-N^2=|\psi_{cas}|^4[ch(2\phi)^2-sh(2\phi)^2]=|\psi_{cas}|^4$$

Therefore, $|\psi_{cas}|=(M^2-N^2)^{1/4}$, and by substituting symbols M and N into a content of formula (19), formula (21) may be obtained:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) - a_5 a_7 \sin(\varphi_5 - \varphi_7)}{2}\right]^2}, \quad (21)$$

A result of formula (21) is the modulus value $|\psi_{cas}(x, y, z)|$ of the first hypercomplex signal. Elements representing the modulus value come from calculations of formula (8) to formula (11). The calculations are calculation processes that can be implemented in engineering. Input information is modulus values $\alpha_1(x, y, z)$, $\alpha_3(x, y, z)$, $\alpha_5(x, y, z)$, and $\alpha_7(x, y, z)$ and angles $\varphi_1(x, y, z)$, $\varphi_3(x, y, z)$, $\varphi_5(x, y, z)$, and $\varphi_7(x, y, z)$ of polar coordinates of formula (8) to formula (11). Output is the modulus value of the first hypercomplex signal, that is, an envelope signal $|\psi_{cas}(x, y, z)|$.

That is to say, in this embodiment of this application, the modulus value of the first hypercomplex signal may be acquired according to the formula (21).

$|\psi_{cas}|$ represents the modulus value of the first hypercomplex signal, $\alpha_1$ is a modulus value of a first analytic signal, $\varphi_i$ is an angle of the first analytic signal, the first analytic signal is an analytic signal that is in the first orthant of 8 orthants in a 3D frequency domain and that corresponds to the input signal, $\alpha_3$ is a modulus value of a third analytic signal, $\varphi_3$ is an angle of the third analytic signal, the third analytic signal is an analytic signal that is in the third orthant of the 8 orthants in the 3D frequency domain and that corresponds to the input signal, $\alpha_5$ is a modulus value of a fifth analytic signal, $\varphi_5$ is an angle of the fifth analytic signal, the fifth analytic signal is an analytic signal that is in the fifth orthant of the 8 orthants in the 3D frequency domain and that corresponds to the input signal, $\alpha_7$ is a modulus value of a seventh analytic signal, $\varphi_7$ is an angle of the seventh analytic signal, the seventh analytic signal is an analytic signal that is in the seventh orthant of the 8 orthants in the 3D frequency domain and that corresponds to the input signal, and the plurality of analytic signals include the first analytic signal, the third analytic signal, the fifth analytic signal, and the seventh analytic signal.

After acquiring the modulus value of the first hypercomplex signal shown in formula (21), the envelope information used for indicating the to-be-detected object in the 3D ultrasound image may be obtained. In this embodiment of this application, the 3D ultrasound image may be generated according to the envelope information. A process of generating the 3D ultrasound image according to the envelope information is not specifically limited herein, and may specifically include, but is not limited to, image processing means such as denoising.

In the technical solution provided in step S206, after generating the 3D ultrasound image, the 3D ultrasound image may be displayed on a display device and/or the envelope information in the 3D ultrasound image is displayed on the display device. The display device and the detection device may form an integral structure, or the display device and the detection device may be separate components. When the display device and the detection device are independent of each other, after the detection device generates the 3D ultrasound image, the 3D ultrasound image may be sent to the display device for displaying, so that a user may observe the to-be-detected object from the display device clearly and intuitively.

Using the ultrasound image display method in this embodiment of this application, because the envelope information used for indicating the to-be-detected object in the 3D ultrasound image is obtained by performing a modulus calculation on the 3D RF signal, but not obtained by splicing the one-dimensional envelope information, the brightness and definition of the to-be-detected object indicated by the envelope information in the 3D ultrasound image are greater than the brightness and definition of the to-be-detected object in a one-dimensional ultrasound image or a two-dimensional ultrasound image. Therefore, this embodiment of this application may make the to-be-detected object be more clearly displayed in the 3D ultrasound image, thereby improving the accuracy of the 3D ultrasound image.

The ultrasound image display method provided in this application may be used to direct 3D envelope detection of the B-mode ultrasound image. In this application, based on a form of 3D convolution and a form of Clifford algebra biquaternion, an analytic signal of high-dimensional hypercomplex numbers is defined to calculate the 3D amplitude of the 3D RF signal at a time, that is, the 3D ultrasound image of the 3D RF signal. The Hilbert transform is used to implement an engineering implementation method for the provided hypercomplex signal and its modulus value. Compared with a conventional method for reconstructing a B-mode ultrasound image by splicing one-dimensional envelope signals of one-dimensional ultrasound RF signals according to spatial positions, this application completely abandons the method for obtaining a B-mode ultrasound image by splicing one-dimensional envelope signals, to avoid a reconstruction error of the 3D B-mode ultrasound image that is formed by splicing the one-dimensional envelope signals. In addition, this application is further applicable to one-time envelope detection of a two-dimensional B-mode ultrasound image and a 3D B-mode ultrasound image.

This application may be applied to a device that performs an envelope calculation on the 3D RF signal, for example, applied to B-mode imaging of a 3D ultrasound device. As shown in FIG. 3, in the 3D B-mode image acquired by using a 3D fan-shaped probe, the method may implement one-time imaging on the 3D data.

This application may implement the modulus calculation on a 3D RF ultrasound signal, to acquire a 3D envelope image thereof (that is, the image indicated by the envelope information in the foregoing embodiment of this application). The modulus value of the 3D RF ultrasound signal herein refers to the 3D envelope image. On the basis of the 3D envelope image, 3D ultrasound image may be obtained by using any two-dimensional or 3D image post-processing algorithm.

Figure 5:
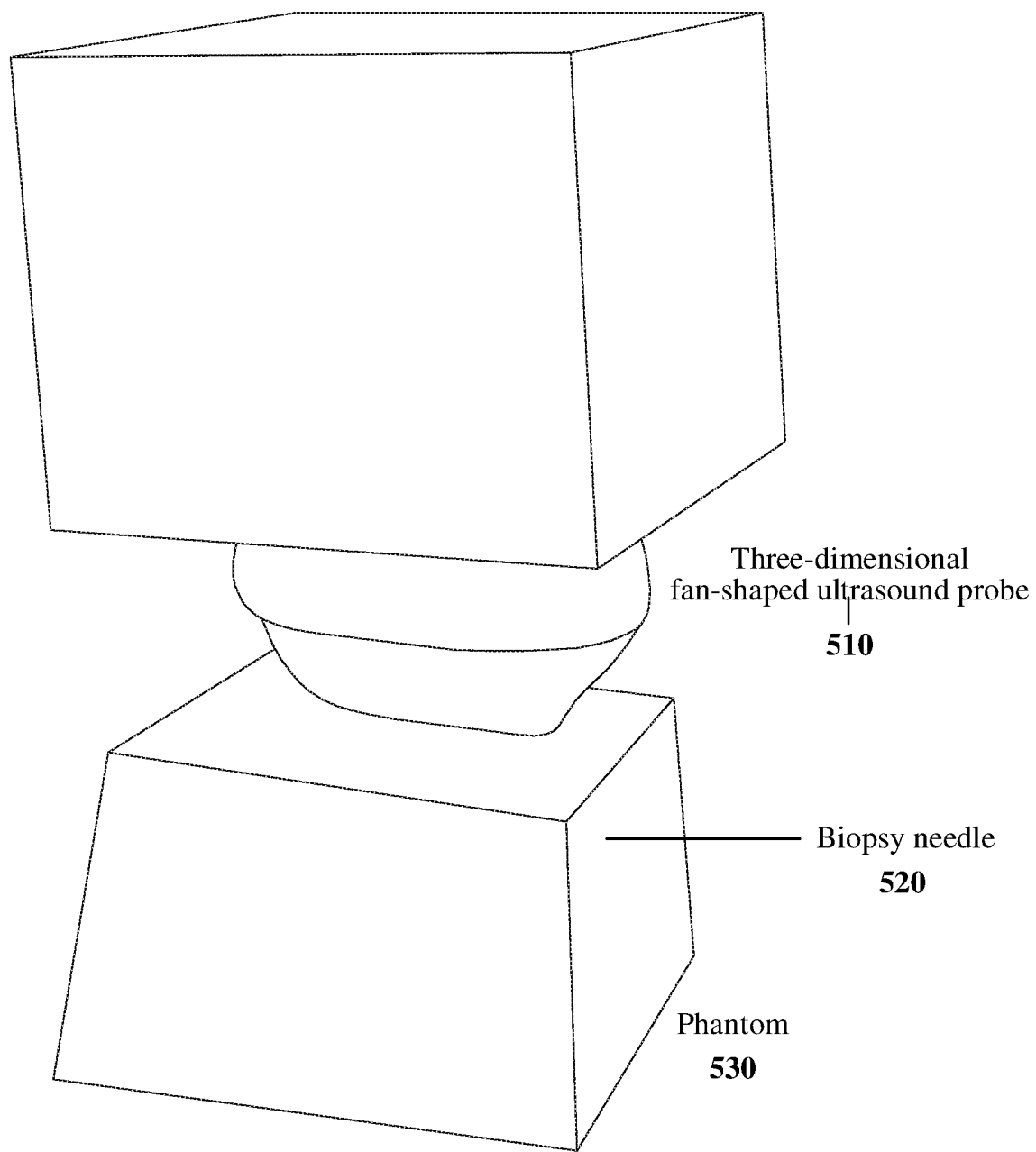
FIG. 5 is a schematic diagram of a platform where a three-dimensional (3D) radio-frequency (RF) signal is collected according to an embodiment of this application.

As shown in FIG. 5, a platform where a 3D fan-shaped ultrasound probe 510 is used to acquire a 3D RF signal is described by using an example. A phantom 530 is under the 3D fan-shaped ultrasound probe to imitate a human body. A biopsy needle 520 is inserted into the phantom 530 to imitate an experiment of inserting the biopsy needle into the human body to acquire human tissue for a subsequent biopsy. In a process of acquiring the human tissue by the biopsy needle, a doctor uses the ultrasound probe to observe a location of the biopsy needle in the human body, aiming to make a needle of the probe reach a predetermined tissue location.

Figure 6:
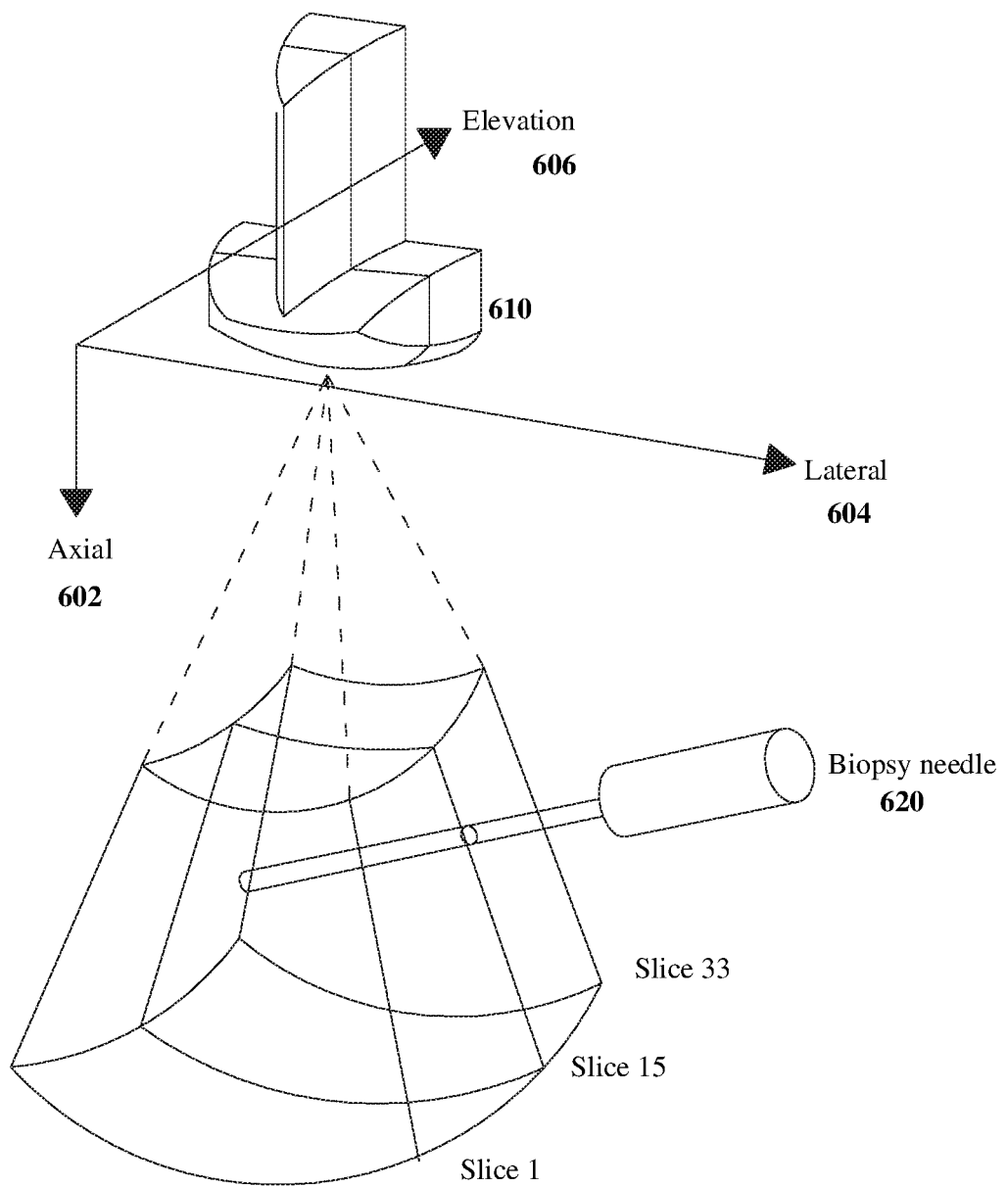
FIG. 6 is a structural diagram of a 3D RF signal according to an embodiment of this application.
Figure 7:
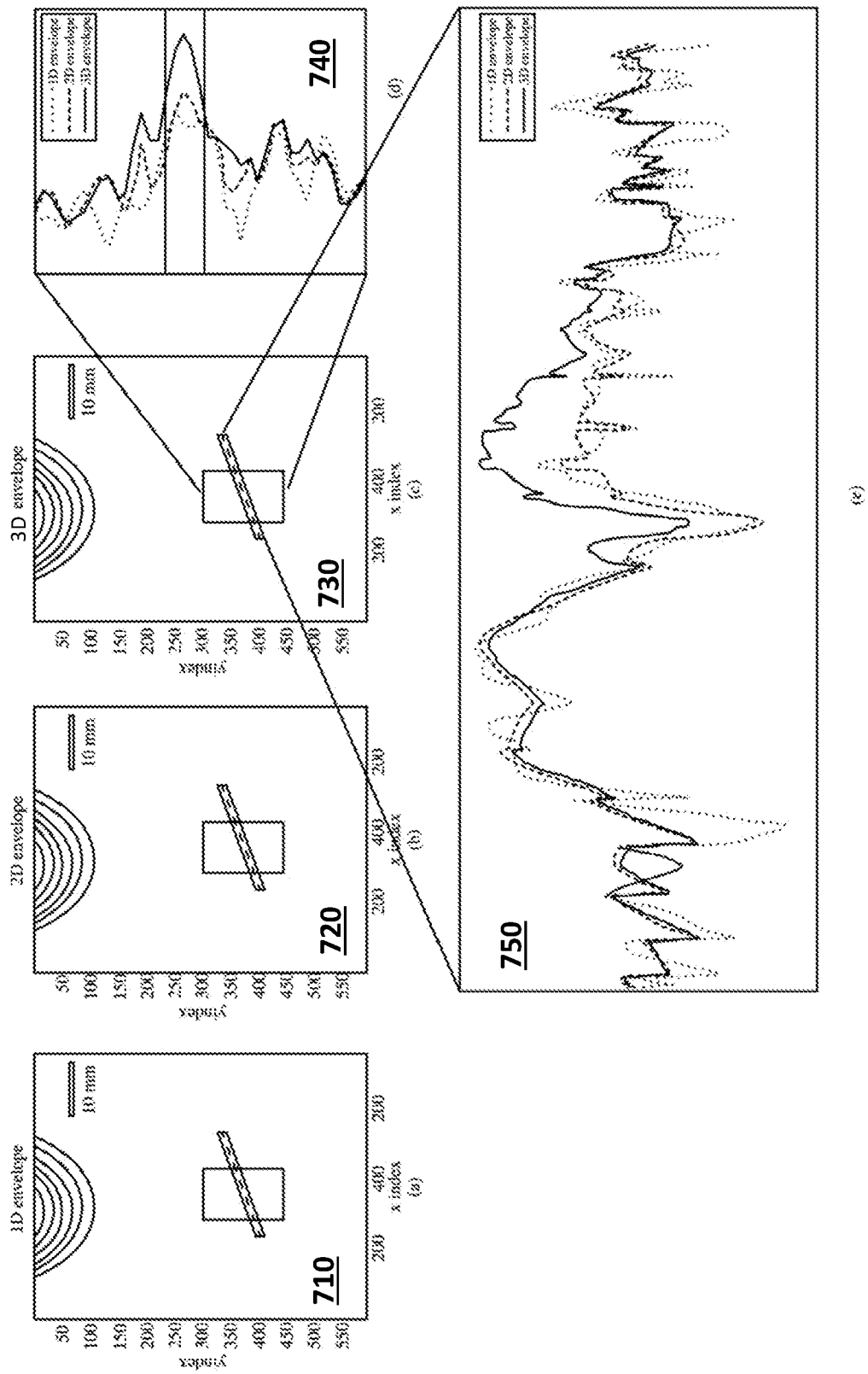
FIG. 7 is a comparison diagram of an envelope image in a 3D ultrasound image according to an embodiment of this application.

FIG. 6 is marked with 3 terms of coordinate axis directions used in the 3D ultrasound: axial 602, lateral 604, and elevation 606. FIG. 6 also shows a ultrasound probe 610 and a biopsy needle 620. In FIG. 6, the x axis and the y axis of the 3D RF signal form a slice. The z axis is an elevation axis that represents a different two-dimensional slice. The ultrasound envelope image of the 3D RF signal acquired in FIG. 6 is calculated separately by using the existing methods and the method provided in this application. FIG. 7 shows a part of the result, which is a result of slice 15 in FIG. 6. The location of the biopsy needle is on the slice. Charts 710 and 720 are results calculated by using the existing one-dimensional method and two-dimensional method. Chart 730 is a result calculated by using the method for this application. In chart 730, a white area that is highlighted, diagonal, long and thin is the location of the biopsy needle. The higher brightness indicates that the biopsy needle is more apparently displayed on the ultrasound envelope image. In order to compare details, chart 740 acquires profiles in a vertical direction of the image. Chart 750 is profiles along the direction of the probe. Higher values of the profiles indicate that the brightness is higher, that is, the probe is more clearly displayed on the envelope image. It can be seen from the values of the profiles that, the brightness in the 3D method provided in this application in the location of the probe is mostly higher than those in the one-dimensional method and/or the two-dimensional method.

Figure 8:
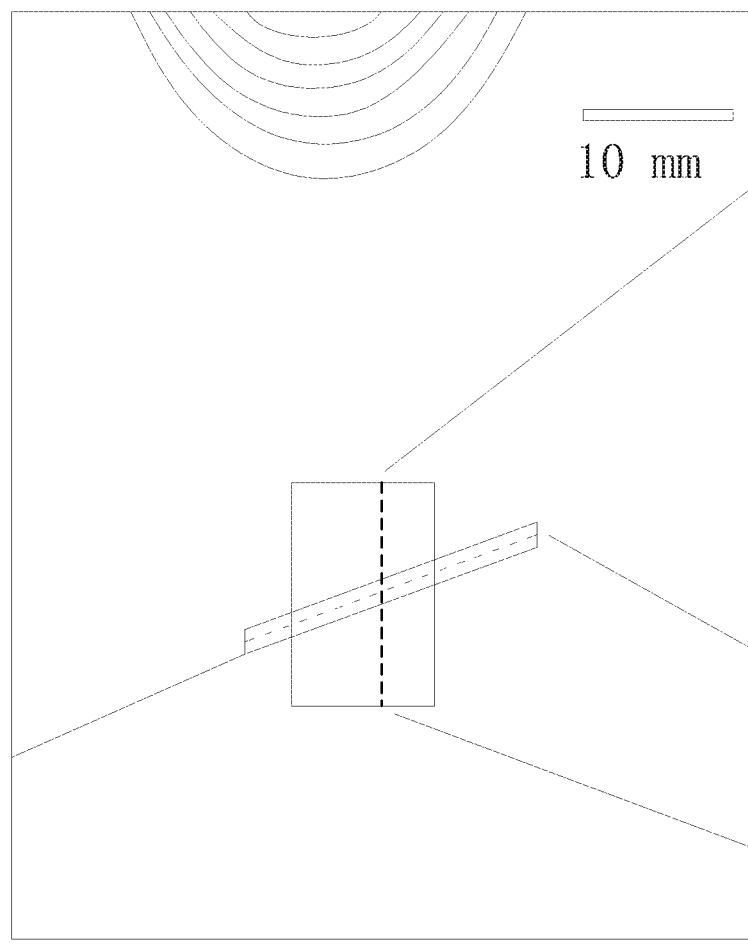
FIG. 8 is an enlarged schematic diagram of an envelope image in a 3D ultrasound image according to an embodiment of this application.

FIG. 8 is enlarged chart 730. In FIG. 8, a diagonal quadrangular box is the location of the biopsy needle. Two imaginary lines are locations of the profiles in chart 740 and chart 750.

Figure 9:
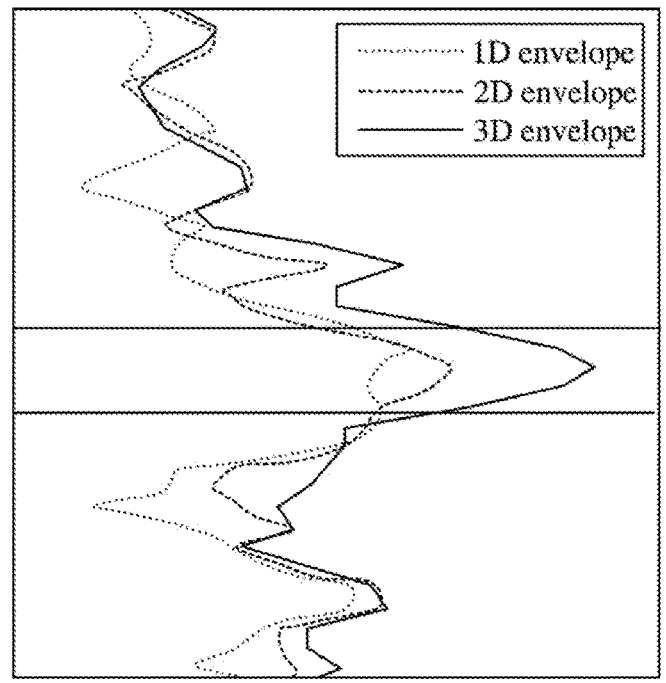
FIG. 9 is an enlarged schematic diagram of a brightness comparison in the vertical direction according to an embodiment of this application.
Figure 10:
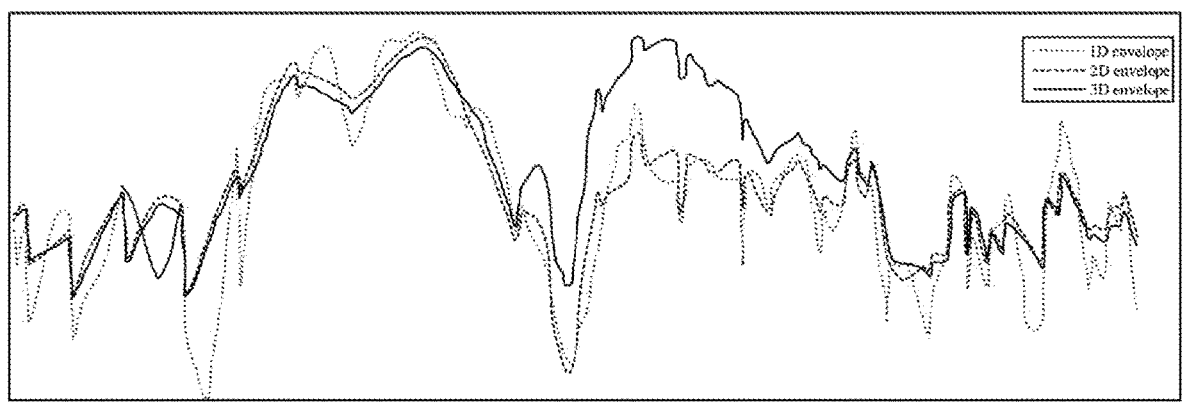
FIG. 10 is an enlarged schematic diagram of a brightness comparison in the biopsy needle direction according to an embodiment of this application.

FIG. 9 is enlarged chart 740. FIG. 10 is enlarged chart 750. The middle of two horizontal lines in FIG. 9 is the location of the biopsy needle. The foregoing examples are two results based on the 3D RF data of the fan-shaped ultrasound probe.

In order to prove the universality of this application, the following example is a calculation of the 3D envelope image based on the 3D RF data of the linear probe. A similar conclusion may also be drawn: the 3D envelope image of the solution can better display location information of the needle.

Figure 11:
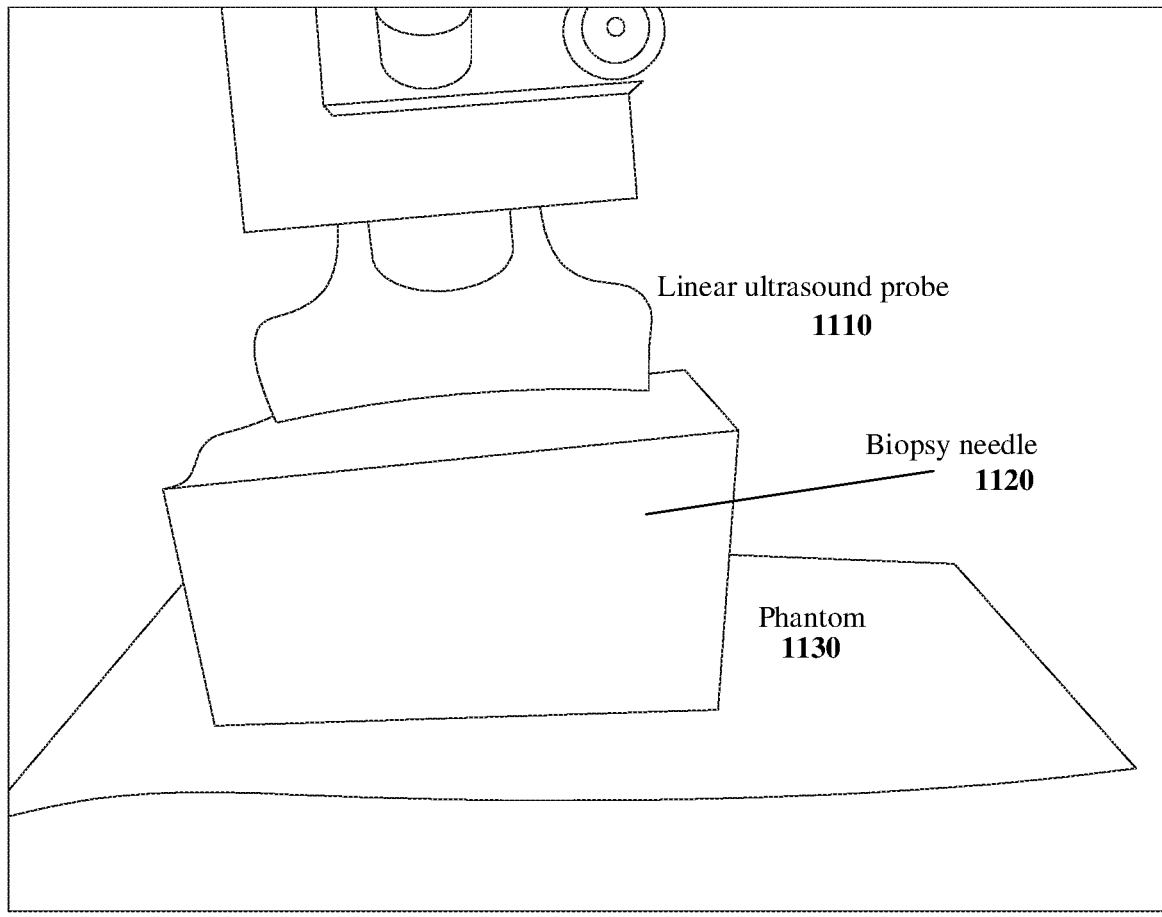
FIG. 11 is a schematic diagram of a platform where a 3D RF signal is collected by a linear probe according to an embodiment of this application.
Figure 12:
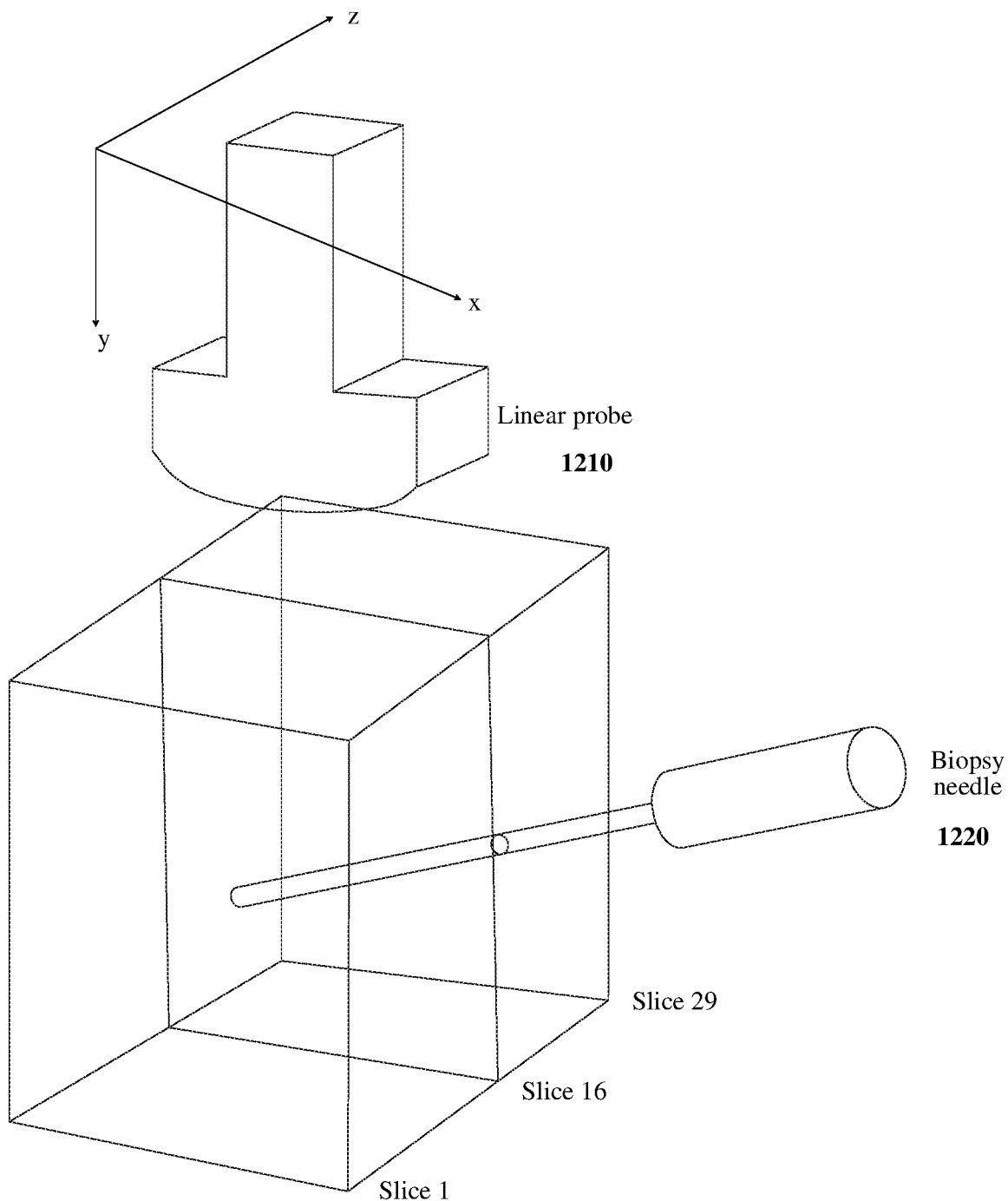
FIG. 12 is a structural diagram of a 3D RF signal collected by a linear probe according to an embodiment of this application.
Figure 13:
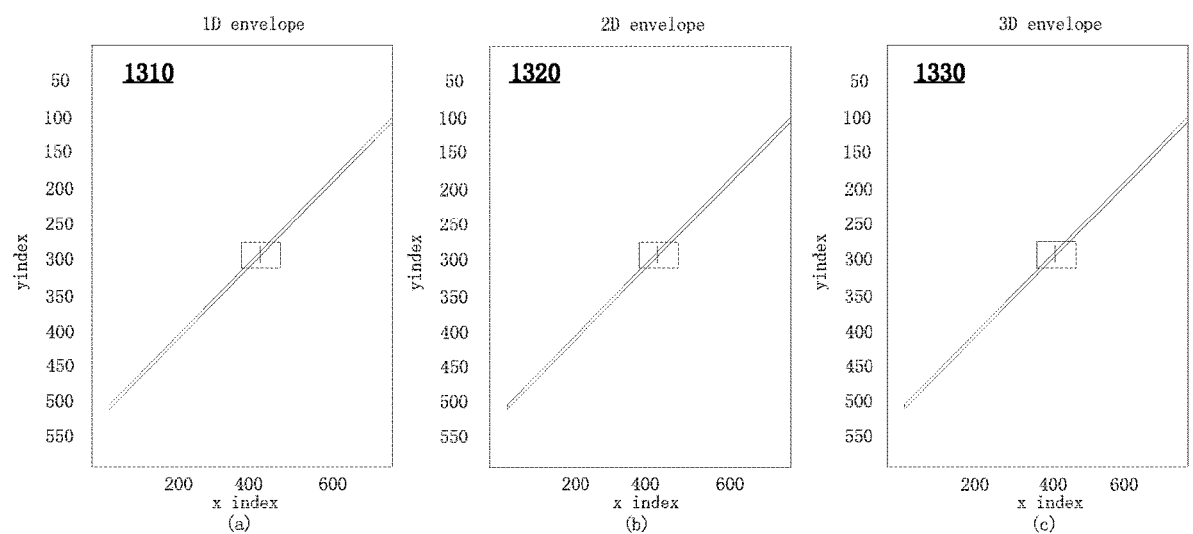
FIG. 13 is a comparison diagram of an envelope image in a 3D ultrasound image collected by a linear probe according to an embodiment of this application.
Figure 14:
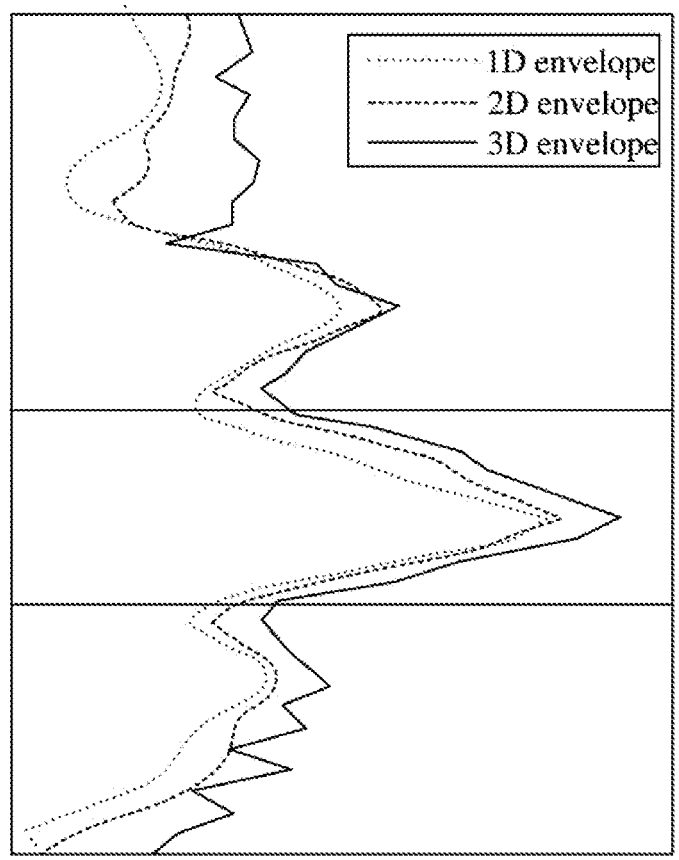
FIG. 14 is a schematic diagram of a brightness comparison of an envelope image in the vertical direction in a 3D ultrasound image collected by a linear probe according to an embodiment of this application.
Figure 15:
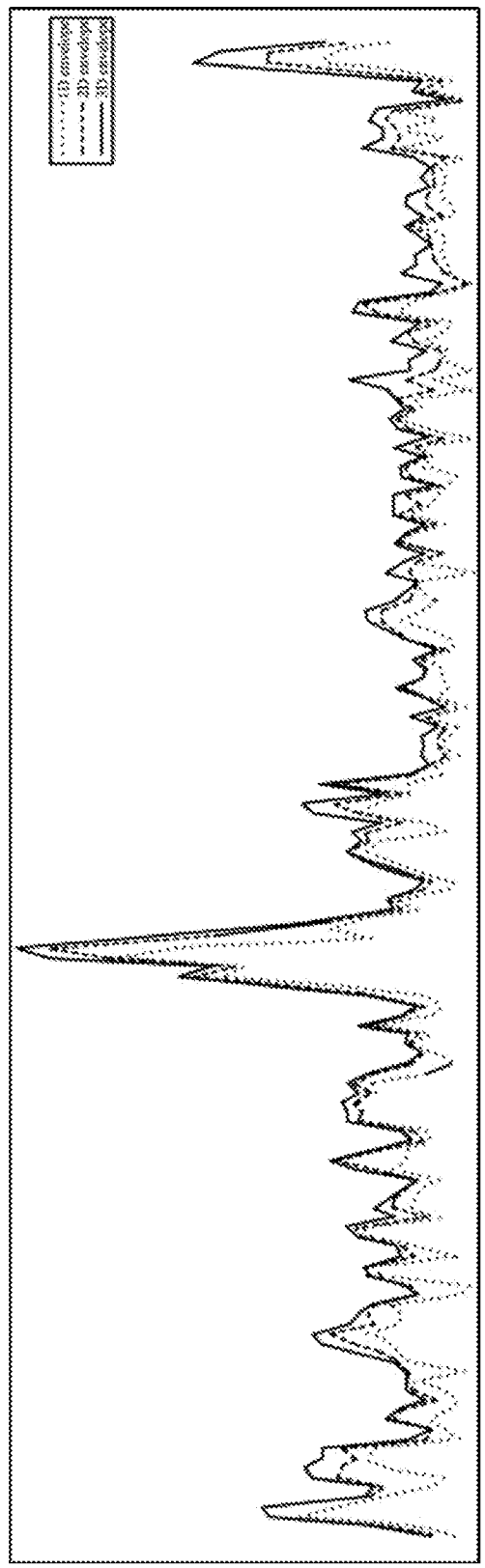
FIG. 15 is a schematic diagram of a brightness comparison of an envelope image in the biopsy needle direction in a 3D ultrasound image collected by a linear probe according to an embodiment of this application.

FIG. 11 is a schematic diagram of a linear ultrasound probe 1110. FIG. 11 also shows a biopsy needle 1120 and a phantom 1130. FIG. 12 is a coordinate axis example of data acquired by the linear ultrasound probe 1210, and the data is in a cubic structure including a plurality of slices, for example, slice 1, slice 16, and slice 29. FIG. 13 is a result of a 3D envelope of the linear ultrasound probe. Chart 1310 is a result of the one-dimensional method, chart 1320 is a result of the two-dimensional method, and chart 1330 is a result of the method of this application. FIG. 14 is a brightness comparison of pixels of the profiles in a vertical direction in the quadrangle. The middle of two horizontal lines is the location of the biopsy needle. The brightness of the result of the 3D method is the highest. The needle is displayed most apparently. FIG. 15 is a brightness comparison of pixels of the profiles along the direction of the needle in the quadrangle. The whole curve is the location of the biopsy needle in the image. The brightness of the result of the 3D method is the highest, and the needle is displayed most apparently.

The solution of this application may solve every envelope calculation of the 3D high-frequency signal mathematically. At an application level, the solution may also solve the problem that the 3D signal is a high-frequency signal in one dimension or two dimensions but not a high-frequency signal in other dimensions. Therefore, the solution can be potentially applied to various physics and engineering application problems related to a modulus value calculation of 3D high-frequency signals, such as, high-frequency signal communications, high-frequency radar signal demodulation, encryption of images by using high-frequency information, and decryption requiring a calculation of envelope information of signals.

To make the description simple, the foregoing method embodiments are stated as a series of action combinations. However, a person skilled in the art needs to know that this application is not limited on the described sequence of the actions because according to this application, certain steps may use another sequence or may be simultaneously performed. In addition, it is to be understood by a person skilled in the art that the embodiments described in the specification all belong to exemplary embodiments and the actions and modules are not mandatory to this application.

According to the foregoing descriptions of implementations, a person skilled in the art may clearly learn that the method according to the foregoing embodiments may be implemented by using software and a necessary general hardware platform, or certainly may be implemented by using hardware. However, in most cases, the former is a better implementation. Based on such an understanding, the technical solutions in this application essentially or the part contributing on the related art may be implemented in the form of a software product. The computer software product is stored in a storage medium (such as a read-only memory (ROM)/random access memory (RAM), a magnetic disk, or an optical disc), and includes several instructions for instructing a terminal device (which may be a mobile phone, a computer, a server, a network device, and the like) to perform the method described in the embodiments of this application.

Figure 16:
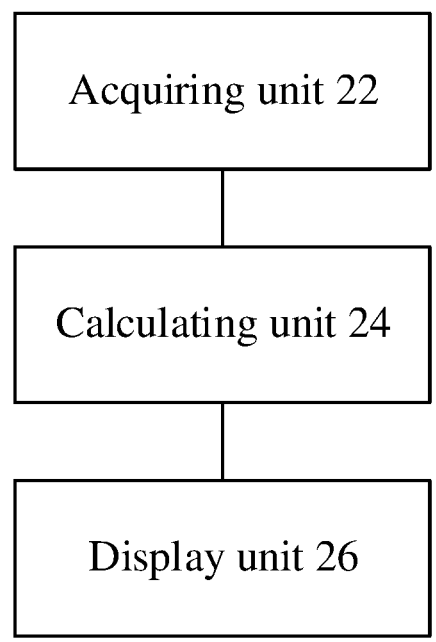
FIG. 16 is a schematic diagram of an optional ultrasound image display apparatus according to an embodiment of this application.

According to another aspect of the embodiments of this application, an ultrasound image display apparatus for implementing the ultrasound image display method is further provided. FIG. 16 is a schematic diagram of an optional ultrasound image display apparatus according to an embodiment of this application. As shown in FIG. 16, the apparatus may include:

an acquiring unit 22, configured to acquire an input signal obtained by performing detection on a to-be-detected object by a detection device, the input signal being a 3D RF signal; a calculating unit 24, configured to perform a modulus calculation on the 3D RF signal to obtain envelope information in a 3D ultrasound image, the modulus calculation being at least used for directly acquiring a 3D amplitude of the 3D RF signal; and a display unit 26, configured to display the envelope information in the 3D ultrasound image on a display device, the envelope information being used for indicating the to-be-detected object.

The acquiring unit 22 in this embodiment may be configured to perform step S202 in the embodiments of this application, the calculating unit 24 in this embodiment may be configured to perform step S204 in the embodiments of this application, and the display unit 26 in this embodiment may be configured to perform step S206 in the embodiments of this application.

Implemented examples and application scenarios of the foregoing modules are the same as those of the corresponding steps, but are not limited to the content disclosed in the foregoing embodiments. The foregoing modules may be run in the hardware environment shown in FIG. 1 as a part of the apparatus, and may be implemented by software, or may be implemented by hardware.

Optionally, the calculating unit 24 may include: a first acquiring module, configured to acquire a first hypercomplex signal corresponding to the 3D RF signal, the first hypercomplex signal being a sum of 8 components, and each component being represented by modulus values and angles of a plurality of analytic signals corresponding to the input signal; and a second acquiring module, configured to acquire a modulus value of the first hypercomplex signal, the modulus value of the first hypercomplex signal being used for representing the 3D amplitude of the 3D RF signal, and envelope information including the modulus value of the first hypercomplex signal.

Optionally, the first acquiring module may include: a first acquiring submodule, configured to acquire a second hypercomplex signal corresponding to the 3D RF signal, the second hypercomplex signal including 8 components, and each component being represented by the Hilbert transform of the input signal; a second acquiring submodule, configured to acquire a correspondence between the components represented by the Hilbert transform and the modulus values and angles of the plurality of analytic signals; and a transforming module, configured to transform the second hypercomplex signal into the first hypercomplex signal according to the correspondence.

Optionally, the second acquiring module is configured to acquire the modulus value of the first hypercomplex signal according to the following formula:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) - a_5 a_7 \sin(\varphi_5 - \varphi_7)}{2}\right]^2}$$

$|\psi_{cas}|$ represents the modulus value of the first hypercomplex signal, $\alpha_1$ is a modulus value of a first analytic signal, $\varphi_1$ is an angle of the first analytic signal, the first analytic signal is an analytic signal that is in the first orthant of 8 orthants in a 3D frequency domain and that corresponds to the input signal, $\alpha_3$ is a modulus value of a third analytic signal, $\varphi_3$ is an angle of the third analytic signal, the third analytic signal is an analytic signal that is in the third orthant of the 8 orthants in the 3D frequency domain and that corresponds to the input signal, $\alpha_5$ is a modulus value of a fifth analytic signal, $\varphi_5$ is an angle of the fifth analytic signal, the fifth analytic signal is an analytic signal that is in the fifth orthant of the 8 orthants in the 3D frequency domain and that corresponds to the input signal, $\alpha_7$ is a modulus value of a seventh analytic signal, $\varphi_7$ is an angle of the seventh analytic signal, the seventh analytic signal is an analytic signal that is in the seventh orthant of the 8 orthants in the 3D frequency domain and that corresponds to the input signal, and the plurality of analytic signals include the first analytic signal, the third analytic signal, the fifth analytic signal, and the seventh analytic signal.

Optionally, the brightness of the to-be-detected object indicated by the envelope information in the 3D ultrasound image is greater than the brightness of the to-be-detected object in a one-dimensional ultrasound image or a two-dimensional ultrasound image.

Implemented examples and application scenarios of the foregoing modules are the same as those of the corresponding steps, but are not limited to the content disclosed in the foregoing embodiments. The foregoing modules may be run in the hardware environment shown in FIG. 1 as a part of the apparatus, and may be implemented by software, or may be implemented by hardware.

Through the foregoing modules, the to-be-detected object is accurately displayed in the 3D ultrasound image, to achieve a technical effect of improving the accuracy of the 3D ultrasound image, thereby solving the technical problem that the 3D B-mode ultrasound image reconstructed in the related art has a reconstruction error that reduces the accuracy of the 3D B-mode ultrasound image.

According to still another aspect of the embodiments of this application, an electronic device for implementing the ultrasound image display method is further provided.

Figure 17:
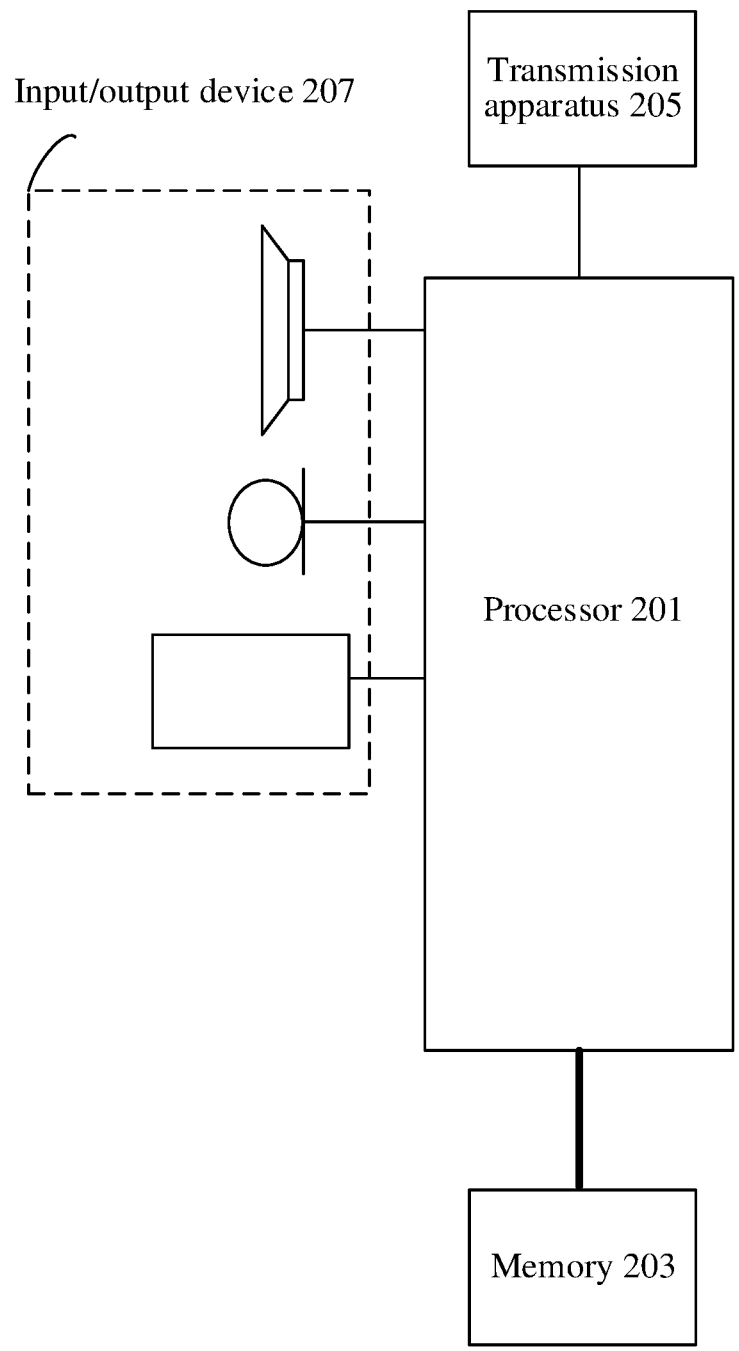
FIG. 17 is a structural block diagram of an electronic device according to an embodiment of this application.

FIG. 17 is a structural block diagram of an electronic device according to an embodiment of this application. As shown in FIG. 17, the electronic device may include: one or more (only one processor is shown in the figure) processors 201 and a memory 203, the memory 203 storing a computer program, and the processor 201 being configured to run the computer program to perform the ultrasound image display method according to the embodiments of this application.

The memory 203 may be configured to store a computer program and a module, for example, a program instruction/module corresponding to the ultrasound image display method and apparatus in the embodiments of this application, and the processor 201 performs various functional applications and data processing by running the computer program and the module stored in the memory 203, that is, implementing the foregoing ultrasound image display method. The memory 203 may include a high-speed random access memory, and may further include a non-volatile memory, for example, one or more magnetic storage apparatuses, flash memories, or other non-volatile solid-state memories. In some embodiments, the memory 203 may further include memories that are remotely disposed relative to the processor 201, and the remote memories may be connected to a terminal via a network. Examples of the network include, but are not limited to, the Internet, an intranet, a local area network, a mobile communications network, and a combination thereof.

Optionally, as shown in FIG. 17, the electronic device may further include: a transmission apparatus 205 and an input/output device 207. The transmission apparatus 205 is configured to receive or send data through a network. Specific instances of the foregoing network may include a wired network and a wireless network. In an example, the transmission apparatus 205 includes a network interface controller (NIC), and the network interface controller may be connected to another network device or a router by using a network cable, so as to communicate with the Internet or a local area network. In an example, the transmission apparatus 205 is a radio frequency (RF) module, and the radio frequency module is configured to communicate with the Internet in a wireless manner.

A person of ordinary skill in the art may understand that, the structure shown in FIG. 17 is only schematic. The electronic device may be a terminal device such as a smartphone (such as an Android mobile phone or an iOS mobile phone), a tablet computer, a palmtop computer, a mobile Internet device (MID), or a PAD. FIG. 17 does not constitute a limitation on a structure of the foregoing electronic device. For example, the electronic device may further include more or fewer components (for example, a network interface and a display apparatus) than those shown in FIG. 17, or has a configuration different from that shown in FIG. 17.

Optionally, in this embodiment, the memory 203 may be configured to store the computer program.

Optionally, in this embodiment, the processor is configured to run the computer program for performing the following steps: acquiring an input signal obtained by performing detection on a to-be-detected object by a detection device, the input signal being a 3D RF signal; performing a modulus calculation on the 3D RF signal to obtain envelope information in a 3D ultrasound image, the modulus calculation being at least used for directly acquiring a 3D amplitude of the 3D RF signal; and displaying the envelope information in the 3D ultrasound image on the display device, the envelope information being used for indicating the to-be-detected object.

The processor 201 is further configured to perform the following steps: acquiring a first hypercomplex signal corresponding to the 3D RF signal, the first hypercomplex signal being a sum of 8 components, and each component being represented by modulus values and angles of a plurality of analytic signals corresponding to the input signal; and acquiring a modulus value of the first hypercomplex signal, the modulus value of the first hypercomplex signal being used for representing the 3D amplitude of the 3D RF signal, and envelope information including the modulus value of the first hypercomplex signal.

The processor 201 is further configured to perform the following steps: acquiring a second hypercomplex signal corresponding to the 3D RF signal, the second hypercomplex signal including 8 components, and each component being represented by the Hilbert transform of the input signal; acquiring a correspondence between the components represented by the Hilbert transform and the modulus values and angles of the plurality of analytic signals; and transforming the second hypercomplex signal into the first hypercomplex signal according to the correspondence.

The processor 201 is further configured to perform the following step: acquiring the modulus value of the first hypercomplex signal according to the following formula:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) -}{\frac{a_5 a_7 \sin(\varphi_5 - \varphi_7)}{2}}\right]^2}$$

$|\psi_{cas}|$ represents the modulus value of the first hypercomplex signal, $\alpha_1$ is a modulus value of a first analytic signal, $\varphi_1$ is an angle of the first analytic signal, the first analytic signal is an analytic signal that is in the first orthant of 8 orthants in a 3D frequency domain and that corresponds to the input signal, $\alpha_3$ is a modulus value of a third analytic signal, $\varphi_3$ is an angle of the third analytic signal, the third analytic signal is an analytic signal that is in the third orthant of the 8 orthants in the 3D frequency domain and that corresponds to the input signal, $\alpha_5$ is a modulus value of a fifth analytic signal, $\varphi_5$ is an angle of the fifth analytic signal, the fifth analytic signal is an analytic signal that is in the fifth orthant of the 8 orthants in the 3D frequency domain and that corresponds to the input signal, $\alpha_7$ is a modulus value of a seventh analytic signal, $\varphi_7$ is an angle of the seventh analytic signal, the seventh analytic signal is an analytic signal that is in the seventh orthant of the 8 orthants in the 3D frequency domain and that corresponds to the input signal, and the plurality of analytic signals include the first analytic signal, the third analytic signal, the fifth analytic signal, and the seventh analytic signal.

Optionally, for a specific example in this embodiment, reference may be made to the example described in the foregoing embodiment, and details are not described herein again in this embodiment.

By using this embodiment of this application, an ultrasound image display solution is provided. By acquiring the input signal obtained by performing the detection on the to-be-detected object by the detection device, the input signal being the 3D RF signal; performing the modulus calculation on the 3D RF signal to obtain the envelope information in the 3D ultrasound image, the modulus calculation being at least used for directly acquiring the 3D amplitude of the 3D RF signal; and displaying the envelope information in the 3D ultrasound image on the display device, the envelope information being used for indicating the to-be-detected object, the to-be-detected object is accurately displayed in the 3D ultrasound image, to achieve a technical effect of improving the accuracy of the 3D ultrasound image, thereby solving the technical problem that the 3D B-mode ultrasound image reconstructed in the related art has a reconstruction error that reduces the accuracy of the 3D B-mode ultrasound image.

According to still another aspect of the embodiments of this application, a storage medium is further provided. The storage medium stores a computer program, the computer program being configured to perform a step of an ultrasound image display method in the foregoing embodiment when being run.

Optionally, in this embodiment, the storage medium may be located in at least one network device of a plurality of network devices in a network shown in the foregoing embodiments.

Optionally, in this embodiment, the storage medium is configured to store the computer program for performing the following steps:

S1. Acquire an input signal obtained by performing detection on a to-be-detected object by a detection device, the input signal being a 3D RF signal.

S2. Perform a modulus calculation on the 3D RF signal to obtain envelope information in a 3D ultrasound image, the modulus calculation being at least used for directly acquiring a 3D amplitude of the 3D RF signal.

S3. Display the envelope information in the 3D ultrasound image on a display device, the envelope information being used for indicating the to-be-detected object.

Optionally, the storage medium is further configured to store the computer program for performing the following steps: acquiring a first hypercomplex signal corresponding to the 3D RF signal, the first hypercomplex signal being a sum of 8 components, and each component being represented by modulus values and angles of a plurality of analytic signals corresponding to the input signal; and acquiring a modulus value of the first hypercomplex signal, the modulus value of the first hypercomplex signal being used for representing the 3D amplitude of the 3D RF signal, and envelope information including the modulus value of the first hypercomplex signal.

Optionally, the storage medium is further configured to store the computer program for performing the following steps: acquiring a second hypercomplex signal corresponding to the 3D RF signal, the second hypercomplex signal including 8 components, and each component being represented by the Hilbert transform of the input signal; acquiring a correspondence between the components represented by the Hilbert transform and the modulus values and angles of the plurality of analytic signals; and transforming the second hypercomplex signal into the first hypercomplex signal according to the correspondence.

Optionally, the storage medium is further configured to store the computer program for performing the following step: acquiring the modulus value of the first hypercomplex signal according to the following formula:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) -}{\frac{a_5 a_7 \sin(\varphi_5 - \varphi_7)}{2}}\right]^2}$$

$|\psi_{cas}|$ represents the modulus value of the first hypercomplex signal, $\alpha_1$ is a modulus value of a first analytic signal, $\varphi_i$ is an angle of the first analytic signal, the first analytic signal is an analytic signal that is in the first orthant of 8 orthants in a 3D frequency domain and that corresponds to the input signal, $\alpha_3$ is a modulus value of a third analytic signal, $\varphi_3$ is an angle of the third analytic signal, the third analytic signal is an analytic signal that is in the third orthant of the 8 orthants in the 3D frequency domain and that corresponds to the input signal, $\alpha_5$ is a modulus value of a fifth analytic signal, $\varphi_5$ is an angle of the fifth analytic signal, the fifth analytic signal is an analytic signal that is in the fifth orthant of the 8 orthants in the 3D frequency domain and that corresponds to the input signal, $\alpha_7$ is a modulus value of a seventh analytic signal, $\varphi_7$ is an angle of the seventh analytic signal, the seventh analytic signal is an analytic signal that is in the seventh orthant of the 8 orthants in the 3D frequency domain and that corresponds to the input signal, and the plurality of analytic signals include the first analytic signal, the third analytic signal, the fifth analytic signal, and the seventh analytic signal.

Optionally, for a specific example in this embodiment, reference may be made to the example described in the foregoing embodiment, and details are not described herein again in this embodiment.

Optionally, in this embodiment, a person of ordinary skill in the art may understand that all or some of the steps of the methods in the foregoing embodiments may be implemented by a program instructing relevant hardware of the terminal device. The program may be stored in a computer-readable storage medium. The storage medium may include a flash disk, a read-only memory (ROM), a random access memory (RAM), a magnetic disk, an optical disc, and the like.

The sequence numbers of the foregoing embodiments of this application are merely for the convenience of description, and do not imply the preference among the embodiments.

When the integrated unit in the foregoing embodiments is implemented in the form of a software functional unit and sold or used as an independent product, the integrated unit may be stored in the foregoing computer-readable storage medium. Based on such an understanding, the technical solution of this application essentially, or a part contributing to the related art, or all or a part of the technical solution may be implemented in a form of a software product. The computer software product is stored in a storage medium and includes several instructions for instructing one or more computer devices (which may be a personal computer, a server, a network device, or the like) to perform all or some of steps of the methods in the embodiments of this application.

In the foregoing embodiments of this application, descriptions of the embodiments have different emphases. As for parts that are not described in detail in one embodiment, reference can be made to the relevant descriptions of the other embodiments.

In the several embodiments provided in this application, it is understood that the disclosed client may be implemented in other manners. The described apparatus embodiment is merely an example. For example, the unit division is merely logical function division and may be another division in an actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between units or modules may be implemented in electric or other forms.

The units described as separate parts may or may not be physically separate. Parts displayed as units may or may not be physical units, and may be located in one position, or may be distributed on a plurality of network units. Some or all of the units may be selected according to actual requirements to achieve the objectives of the solutions in the embodiments.

In addition, functional units in the embodiments of this application may be integrated into one processing unit, or each of the units may exist alone physically, or two or more units are integrated into one unit. The integrated unit may be implemented in the form of hardware, or may be implemented in the form of a software function unit.

The foregoing descriptions are merely exemplary implementations of this application. A person of ordinary skill in the art may further make several improvements and refinements without departing from the principle of this application, and the improvements and refinements shall fall within the protection scope of this application.

The invention claimed is:

1. A method for displaying an ultrasound image, the method comprising:
   acquiring, by a device comprising a memory storing instructions, and a processor in communication with the memory, an input signal comprising a digital representation of a three-dimensional (3D) radio-frequency (RF) signal obtained from an ultrasound probe by performing detection on a to-be-detected object;
   performing, by the device, a modulus calculation on the 3D RF signal to obtain envelope information in a 3D ultrasound image, the modulus calculation being at least used for directly acquiring a 3D amplitude of the 3D RF signal, by:
      determining, by the device, a first hypercomplex signal corresponding to the 3D RF signal, the first hypercomplex signal being a sum of 8 components, and each component being represented by modulus values and angles of a plurality of analytic signals corresponding to the input signal, and
      determining, by the device, the envelope information comprising a modulus value of the first hypercomplex signal, the modulus value of the first hypecromplex signal being used for representing the 3D amplitude of the 3D RF signal; and
   outputting by the device, a digital representation of the envelope information in the 3D ultrasound image to a display for displaying, the envelope information being at least used for indicating the to-be-detected object,
   wherein the determining the first hyprecomplex signal corresponding to the 3D RF signal comprises:
      acquiring, by the device, a second hypercomplex signal corresponding to the 3D RF signal, the second hypercomplex signal comprising 8 components, and at least one component being represented by a Hilbert transform of the input signal,
      determining, by the device, a correspondence between the components represented by the Hilbert Transform and the modulus values and angles of the plurality of analytic signals, and
      transforming, by the device, the second hypercomplex signal into the first hypercomplex signal according to the correspondence.

2. The method according to claim 1, wherein:
the second hypercomplex signal comprises the following:

$$\psi_{cas}(x, y, z) = f + iH_{yz}\{f\} + j(-H_{xz}\{f\}) +$$
$$kH_{xy}\{f\} + \epsilon(-H\{f\}) + \epsilon i H_x\{f\} + \epsilon j H_y\{f\} + \epsilon k H_z\{f\},$$

wherein $\epsilon$ represents a vector unit, f represents the 3D RF signal f(x, y, z), $H_z\{f\}$ represents a Hilbert transform of the 3D RF signal f(x, y, z) in the z direction, $H_y\{f\}$ represents a Hilbert transform of the 3D RF signal f(x, y, z) in the y direction, $H_x\{f\}$ represents a Hilbert transform of the 3D RF signal f(x, y, z) in the x direction, $H_{yz}\{f\}$ represents a Hilbert transform of the 3D RF signal f(x, y, z) in the y direction and the z direction, $H_{xz}\{f\}$ represents a Hilbert transform of the 3D RF signal f(x, y, z) in the x direction and the z direction, and $H_{xy}\{f\}$ represents a Hilbert transform of the 3D RF signal f(x, y, z) in the x direction and the y direction.

3. The method according to claim 2, wherein:
the correspondence between the components represented by the Hilbert Transform and the modulus values and angles of the plurality of analytic signals comprises the following:

$f=\frac{1}{4}(\alpha_1 \cos \varphi_1 + \alpha_3 \cos \varphi_3 + \alpha_5 \cos \varphi_5 + \alpha_7 \cos \varphi_7)$, $H_{yz}\{f\}=\frac{1}{4}(-\alpha_1 \cos \varphi_1 + \alpha_3 \cos \varphi_3 + \alpha_5 \cos \varphi_5 - \alpha_7 \cos \varphi_7)$, $-H_{xz}\{f\}=\frac{1}{4}(\alpha_1 \cos \varphi_1 + \alpha_3 \cos \varphi_3 - \alpha_5 \cos \varphi_5 - \alpha_7 \cos \varphi_7)$, $H_{xy}\{f\}=\frac{1}{4}(-\alpha_1 \cos \varphi_1 + \alpha_3 \cos \varphi_3 - \alpha_5 \cos \varphi_5 + \alpha_7 \cos \varphi_7)$, $-H\{f\}=\frac{1}{4}(\alpha_1 \sin \varphi_1 - \alpha_3 \sin \varphi_3 - \alpha_5 \sin \varphi_5 + \alpha_7 \sin \varphi_7)$, $H_x\{f\}=\frac{1}{4}(\alpha_1 \sin \varphi_1 + \alpha_3 \sin \varphi_3 + \alpha_5 \sin \varphi_5 + \alpha_7 \sin \varphi_7)$, $H_y\{f\}=\frac{1}{4}(\alpha_1 \sin \varphi_1 - \alpha_3 \sin \varphi_3 + \alpha_5 \sin \varphi_5 - \alpha_7 \sin \varphi_7)$, $H_z\{f\}=\frac{1}{4}(\alpha_1 \sin \varphi_1 + \alpha_3 \sin \varphi_3 - \alpha_5 \sin \varphi_5 - \alpha_7 \sin \varphi_7)$.

$a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, and the seventh analytic signal being an analytic signal that is in the seventh orthant of the 8 orthants in the 3D frequency domain and that corresponds to the input signal.

4. The method according to claim 1, further comprising:
acquiring, by the device, the modulus value of the first hypercomplex signal according to the following:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) - a_5 a_7 \sin(\varphi_5 - \varphi_7)}{2}\right]^2},$$

$|\psi_{cas}|$ representing the modulus value of the first hypercomplex signal, $a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, the seventh analytic signal being an analytic signal that is in the seventh orthant of the 8 orthants in the 3D frequency domain and that corresponds to the input signal, and the plurality of analytic signals comprising the first analytic signal, the third analytic signal, the fifth analytic signal, and the seventh analytic signal.

5. The method according to claim 1, wherein:
a brightness of the to-be-detected object indicated by the envelope information in the 3D ultrasound image is greater than a brightness of the to-be-detected object in a one-dimensional ultrasound image or a two-dimensional ultrasound image.

6. An apparatus for displaying an ultrasound image, the apparatus comprising:
a memory storing instructions; and
a processor in communication with the memory, wherein, when the processor executes the instructions, the processor is configured to cause the apparatus to:
  acquire an input signal comprising a digital representation of a three-dimensional (3D) radio-frequency (RF) signal obtained from an ultrasound probe by performing detection on a to-be-detected object, the input signal,
  perform a modulus calculation on the 3D RF signal to obtain envelope information in a 3D ultrasound image, the modulus calculation being at least used for directly acquiring a 3D amplitude of the 3D RF signal, by:
    determining a first hypercomplex signal corresponding to the 3D RF signal, the first hypercomplex signal being a sum of 8 components, and each component being represented by modulus values and angles of a plurality of analytic signals corresponding to the input signal, and
    determining the envelope information comprising a modulus value of the first hypercomplex signal, the modulus value of the first hypercomplex signal being used for representing the 3D amplitude of the 3D RF signal, and
  output a digital representation of the envelope information in the 3D ultrasound image to a display for displaying, the envelope information being at least used for indicating the to-be-detected object,
wherein the determining the first hypercomplex signal corresponding to the 3D RF signal comprises:
  acquiring a second hypercomplex signal corresponding to the 3D RF signal, the second hypercomplex signal comprising 8 components, and at least one component being represented by a Hilbert transform of the input signal,
  determining a correspondence between the components represented by the Hilbert Transform and the modulus values and angles of the plurality of analytic signals, and
  transforming the second hypercomplex signal into the first hypercomplex signal according to the correspondence.

7. The apparatus according to claim 6, wherein:
the second hypercomplex signal comprises the following:

$$\psi_{cas}(x, y, z) = f + iH_{yz}\{f\} + j(-H_{xz}\{f\}) + kH_{xy}\{f\} + \epsilon(-H\{f\}) + \epsilon iH_x\{f\} + \epsilon jH_y\{f\} + \epsilon kH_z\{f\},$$

wherein $\epsilon$ represents a vector unit, f represents the 3D RF signal f(x, y, z), $H_z\{f\}$ represents a Hilbert transform of the 3D RF signal f(x, y, z) in the z direction, $H_y\{f\}$ represents a Hilbert transform of the 3D RF signal f(x, y, z) in the y direction, $H_x\{f\}$ represents a Hilbert transform of the 3D RF signal f(x, y, z) in the x direction, $H_y\{f\}$ represents a Hilbert transform of the 3D RF signal f(x, y, z) in the y direction and the z direction, $H_{xz}\{f\}$ represents a Hilbert transform of the 3D RF signal f(x, y, z) in the x direction and the z direction, and $H_{xy}\{f\}$ represents a Hilbert transform of the 3D RF signal f(x, y, z) in the x direction and the y direction.

8. The apparatus according to claim 7, wherein:
the correspondence between the components represented by the Hilbert Transform and the modulus values and angles of the plurality of analytic signals comprises the following:

$f=\frac{1}{4}(\alpha_1 \cos \varphi_1+\alpha_3 \cos \varphi_3+\alpha_5 \cos \varphi_5+\alpha_7 \cos \varphi_7),$ $H_{yz}\{f\}=\frac{1}{4}(-\alpha_1 \cos \varphi_1+\alpha_3 \cos \varphi_3+\alpha_5 \cos \varphi_5-\alpha_7 \cos \varphi_7),$ $-H_{xz}\{f\}=\frac{1}{4}(\alpha_1 \cos \varphi_1+\alpha_3 \cos \varphi_3-\alpha_5 \cos \varphi_5-\alpha_7 \cos \varphi_7),$ $H_{xy}\{f\}=\frac{1}{4}(-\alpha_1 \cos \varphi_1+\alpha_3 \cos \varphi_3-\alpha_5 \cos \varphi_5+\alpha_7 \cos \varphi_7),$ $-H\{f\}=\frac{1}{4}(\alpha_1 \sin \varphi_1-\alpha_3 \sin \varphi_3-\alpha_5 \sin \varphi_5+\alpha_7 \sin \varphi_7),$ $H_x\{f\}=\frac{1}{4}(\alpha_1 \sin \varphi_1+\alpha_3 \sin \varphi_3+\alpha_5 \sin \varphi_5+\alpha_7 \sin \varphi_7),$ $H_y\{f\}=\frac{1}{4}(\alpha_1 \sin \varphi_1-\alpha_3 \sin \varphi_3+\alpha_5 \sin \varphi_5-\alpha_7 \sin \varphi_7),$ $H_z\{f\}=\frac{1}{4}(\alpha_1 \sin \varphi_1+\alpha_3 \sin \varphi_3-\alpha_5 \sin \varphi_5-\alpha_7 \sin \varphi_7).$ $a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, and the seventh analytic signal being an analytic signal that is in the seventh orthant of the 8 orthants in the 3D frequency domain and that corresponds to the input signal.

9. The apparatus according to claim 6, wherein, when the processor executes the instructions, the processor is configured to further cause the apparatus to:
acquire the modulus value of the first hypercomplex signal according to the following:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) - a_5 a_7 \sin(\varphi_5 - \varphi_7)}{2}\right]^2},$$

$|\psi_{cas}|$ representing the modulus value of the first hypercomplex signal, $a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, the seventh analytic signal being an analytic signal that is in the seventh orthant of the 8 orthants in the 3D frequency domain and that corresponds to the input signal, and the plurality of analytic signals comprising the first analytic signal, the third analytic signal, the fifth analytic signal, and the seventh analytic signal.

10. The apparatus according to claim 6, wherein:
a brightness of the to-be-detected object indicated by the envelope information in the 3D ultrasound image is greater than a brightness of the to-be-detected object in a one-dimensional ultrasound image or a two-dimensional ultrasound image.

11. A non-transitory computer readable storage medium storing computer readable instructions, wherein, the computer readable instructions, when executed by a processor, are configured to cause the processor to perform:
acquiring an input signal comprising a digital representation of a three-dimensional (3D) radio-frequency (RF) signal obtained from au ultrasound probe by performing detection on a to-be-detected object;
performing a modulus calculation on the 3D RF signal to obtain envelope information in a 3D ultrasound image, the modulus calculation being at least used for directly acquiring a 3D amplitude of the 3D RF signal, by:
determining a first hypercomplex signal corresponding to the 3D RF signal, the first hypercomplex signal being a sum of 8 components, and each component being represented by modulus values and angles of a plurality of analytic signals corresponding to the input signal, and
determining the envelope information comprising a modulus value of the first hypercomplex signal, the modulus value of the first hypercomplex signal being used for representing the 3D amplitude of the 3D RF signal; and outputting a digital representation of the envelope information in the 3D ultrasound image to a display for displaying, the envelope information being at least used for indicating the to-be-detected object, wherein the determining the first hyprecomplex signal corresponding to the 3D RF signal comprises:

acquiring a second hypercomplex signal corresponding to the 3D RF signal, the second hypercomplex signal comprising 8 components, and at least one component being represented by a Hilbert transform of the input signal, determining a correspondence between the components represented by the Hilbert Transform and the modulus values and angles of the plurality of analytic signals, and transforming the second hyprecomplex signal into the first hypercomplex signal according to the correspondence.

12. The non-transitory computer readable storage medium according to claim 11, wherein:

the second hypercomplex signal comprises the following:

$$\psi_{cas}(x, y, z) = f + iH_{yz}\{f\} + j(-H_{xz}\{f\}) + kH_{xy}\{f\} + \epsilon(-H\{f\}) + \epsilon i H_x\{f\} + \epsilon j H_y\{f\} + \epsilon k H_z\{f\},$$

wherein $\epsilon$ represents a vector unit, f represents the 3D RF signal f(x, y, z), $H_z\{f\}$ represents a Hilbert transform of the 3D RF signal f(x, y, z) in the z direction, $H_y\{f\}$ represents a Hilbert transform of the 3D RF signal f(x, y, z) in the y direction, $H_x\{f\}$ represents a Hilbert transform of the 3D RF signal f(x, y, z) in the x direction, $H_{yz}\{f\}$ represents a Hilbert transform of the 3D RF signal f(x, y, z) in the y direction and the z direction, $H_{xz}\{f\}$ represents a Hilbert transform of the 3D RF signal f(x, y, z) in the x direction and the z direction, and $H_{xy}\{f\}$ represents a Hilbert transform of the 3D RF signal f(x, y, z) in the x direction and the y direction.

13. The non-transitory computer readable storage medium according to claim 12, wherein:

the correspondence between the components represented by the Hilbert Transform and the modulus values and angles of the plurality of analytic signals comprises the following:

$f = \frac{1}{4}(a_1 \cos \varphi_1 + a_3 \cos \varphi_3 + a_5 \cos \varphi_5 + a_7 \cos \varphi_7)$, $H_{yz}\{f\} = \frac{1}{4}(-a_1 \cos \varphi_1 + a_3 \cos \varphi_3 + a_5 \cos \varphi_5 - a_7 \cos \varphi_7)$, $-H_{xz}\{f\} = \frac{1}{4}(a_1 \cos \varphi_1 + a_3 \cos \varphi_3 - a_5 \cos \varphi_5 - a_7 \cos \varphi_7)$, $H_{xy}\{f\} = \frac{1}{4}(-a_1 \cos \varphi_1 + a_3 \cos \varphi_3 - a_5 \cos \varphi_5 + a_7 \cos \varphi_7)$, $-H\{f\} = \frac{1}{4}(a_1 \sin \varphi_1 - a_3 \sin \varphi_3 - a_5 \sin \varphi_5 + a_7 \sin \varphi_7)$, $H_x\{f\} = \frac{1}{4}(a_1 \sin \varphi_1 + a_3 \sin \varphi_3 + a_5 \sin \varphi_5 + a_7 \sin \varphi_7)$, $H_y\{f\} = \frac{1}{4}(a_1 \sin \varphi_1 - a_3 \sin \varphi_3 + a_5 \sin \varphi_5 - a_7 \sin \varphi_7)$, $H_z\{f\} = \frac{1}{4}(a_1 \sin \varphi_1 + a_3 \sin \varphi_3 - a_5 \sin \varphi_5 - a_7 \sin \varphi_7)$, $a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, and the seventh analytic signal being an analytic signal that is in the seventh orthant of the 8 orthants in the 3D frequency domain and that corresponds to the input signal.

14. The non-transitory computer readable storage medium according to claim 11, wherein, the computer readable instructions, when executed by a processor, are configured to further cause the processor to perform:

acquiring the modulus value of the first hypercomplex signal according to the following:

$$|\psi_{cas}| = \sqrt[4]{\left[\frac{a_1^2 + a_3^2 + a_5^2 + a_7^2}{4}\right]^2 - \left[\frac{a_1 a_3 \sin(\varphi_1 - \varphi_3) - a_5 a_7 \sin(\varphi_5 - \varphi_7)}{2}\right]^2},$$

$|\psi_{cas}|$ representing the modulus value of the first hypercomplex signal, $a_1$ being a modulus value of a first analytic signal, $\varphi_1$ being an angle of the first analytic signal, the first analytic signal being an analytic signal that is in the first orthant of 8 orthants in a 3D frequency domain and that corresponds to the input signal, $a_3$ being a modulus value of a third analytic signal, $\varphi_3$ being an angle of the third analytic signal, the third analytic signal being an analytic signal that is in the third orthant of the 8 orthants in the 3D frequency domain and that corresponds to the input signal, $a_5$ being a modulus value of a fifth analytic signal, $\varphi_5$ being an angle of the fifth analytic signal, the fifth analytic signal being an analytic signal that is in the fifth orthant of the 8 orthants in the 3D frequency domain and that corresponds to the input signal, $a_7$ being a modulus value of a seventh analytic signal, $\varphi_7$ being an angle of the seventh analytic signal, the seventh analytic signal being an analytic signal that is in the seventh orthant of the 8 orthants in the 3D frequency domain and that corresponds to the input signal, and the plurality of analytic signals comprising the first analytic signal, the third analytic signal, the fifth analytic signal, and the seventh analytic signal.

* * * * *